(12) United States Patent
Aiba et al.

(10) Patent No.: US 7,871,805 B2
(45) Date of Patent: *Jan. 18, 2011

(54) GLUCOSE DEHYDROGENASE

(75) Inventors: Hiroshi Aiba, Tsuruga (JP); Hiroshi Kawaminami, Tsuruga (JP); Takahide Kishimoto, Tsuruga (JP); Yoshiaki Nishiya, Tsuruga (JP)

(73) Assignee: Toyo Boseki Kabushiki Kaisha, Osaka-shi (JP)

( * ) Notice: Subject to any disclaimer, the term of this patent is extended or adjusted under 35 U.S.C. 154(b) by 49 days.

This patent is subject to a terminal disclaimer.

(21) Appl. No.: 12/351,177

(22) Filed: Jan. 9, 2009

(65) Prior Publication Data

US 2009/0155848 A1 Jun. 18, 2009

Related U.S. Application Data

(62) Division of application No. 11/694,540, filed on Mar. 30, 2007, now Pat. No. 7,494,794.

(60) Provisional application No. 60/788,252, filed on Mar. 31, 2006.

(51) Int. Cl.
 *C12N 9/10* (2006.01)
(52) U.S. Cl. .................................................. 435/193
(58) Field of Classification Search .................. 435/193
 See application file for complete search history.

(56) References Cited

U.S. PATENT DOCUMENTS

| 4,877,733 | A | 10/1989 | Takahashi et al. |
| 5,723,284 | A | 3/1998 | Ye |
| 7,371,836 | B2 | 5/2008 | Desnoyers et al. |
| 2004/0023330 | A1 | 2/2004 | Sode |
| 2006/0063217 | A1 | 3/2006 | Omura et al. |
| 2007/0105174 | A1 | 5/2007 | Aiba |
| 2008/0003628 | A1 | 1/2008 | Kitabayashi et al. |
| 2008/0014611 | A1 | 1/2008 | Kitabayashi et al. |
| 2008/0014612 | A1 | 1/2008 | Tsuji et al. |
| 2008/0020426 | A1 | 1/2008 | Aiba et al. |
| 2008/0090278 | A1 | 4/2008 | Kitabayashi et al. |

FOREIGN PATENT DOCUMENTS

| EP | 0 501 375 A1 | 9/1992 |
| EP | 0 800 086 B1 | 1/2003 |
| EP | 1 584 675 A1 | 10/2005 |
| EP | 1 862 543 A1 | 12/2007 |
| JP | 4-271785 A | 9/1992 |
| JP | 10-010130 A | 1/1998 |
| JP | 10-84954 A | 4/1998 |
| WO | WO 02/36779 A1 | 5/2002 |
| WO | WO 03/012071 A2 | 2/2003 |
| WO | WO 2004-058958 A1 | 7/2004 |
| WO | WO 2006/101239 A1 | 9/2006 |

OTHER PUBLICATIONS

Database UNIPROT, Entry Name "Q2USF2_ASPOR," Accession No. Q2USF2 (Jan. 24, 2006).
Muraya et al., *Fujifilm Research & Development*, 44: 53-59 (1999), English Abstract.
Sode et al., *Biotechnology Techniques*, 11(8): 577-580 (1997).
Terebiznik et al., *Biotechnology Techniques*, 12(9): 683-687 (1998).
Bak et al., *Biochimica et Biophysica Acta*, 139: 265-276 (1967).
Bak, *Biochimica et Biophysica Acta*, 139: 277-293 (1967).
Bak, *Biochimica et Biophysica Acta*, 146: 317-327 (1967).
Bak et al., *Biochimica et Biophysica Acta*, 146: 328-335 (1967).
Belenky et al., *Antibiotiki*, 18: 602-603 (Jul. 1964), English Abstract.
Elzainy et al., *Ann. Microbiol. Enzimol.*, 43: 169-179 (1993).
Müller, *Arch. Microbiol.*, 144: 151-157 (1986).
Scognamiglio et al., *Journal of Fluorescence*, 14(5): 491-498 (Sep. 2004).
Machida et al., *Nature*, 438: 1157-1161 (2005), English Abstract.

*Primary Examiner*—Maryam Monshipouri
(74) *Attorney, Agent, or Firm*—Leydig, Voit & Mayer, Ltd.

(57) ABSTRACT

The present invention provides glucose dehydrogenase which is excellent in heat resistance and substrate specificity and is not affected by dissolved oxygen. Specifically, the present invention relates to glucose dehydrogenase characterized by being derived from an eukaryotic organism and keeping 90% or more activity after being treated with heat at 55° C. for 15 minutes in a liquid form compared with the activity before being treated.

4 Claims, 7 Drawing Sheets

SEQUENCE LISTING

```
<160> NUMBER OF SEQ ID NOS: 6

<210> SEQ ID NO 1
<211> LENGTH: 1773
<212> TYPE: DNA
<213> ORGANISM: Penicillium lilacinoechinulatum

<400> SEQUENCE: 1
atgaggagct tgataagcct agctctcttg cctttggcag ctgcagttcc ccatgtttca      60
cgtagctctg agactacata cgactacatt gtagttggag gtggaactag tggcctggtt     120
atagctaatc gactttctga gcttgaaaaa gtgaatgttc tcgttattga agccggtggc     180
tcagtgtaca acaatcctaa tgtaaccgat accgccggat atggaaaggc ctttggcact     240
gatattgatt gggcatatga gacagtcaag caagaatggg gaggaggtac caaacaaaca     300
gtaagagctg gaaaggctct cggaggtacc tcaaccatca acggaatggt ctatctgcgg     360
gctcagaaaa gtcagatcga tgcgtgggag aagatcggaa atgacggctg gaactggaag     420
aacctgttcc cttactatcg caagggagaa aaatttcaag ttccaaccga ctatgcattt     480
ttggaaggaa ccggcgttgc ctatgatcca gctttccatg ggtataacgg tcctctgaag     540
gtgggctgga cctcaacaca attgaacgat ggccttgccc aagtgatgaa ctctacttac     600
cagaatatgt cggtccctgt cccatacaac aaggatccaa acggtggaca aatggtcgga     660
tactcggttt accccaagac tgtcaactcg gaactcaata ttcgtgagga tgctgccaga     720
gcatactact accctatca aaaccgaacc aaccttcatg tttggcttaa ttctcatgtc     780
aataagcttg tttggaagga tggagccaac atgaccgcag atggcgtgga agtcaagttc     840
tccaacggca caactgctac cgttaaggca gcgcgtgaag tgatccttgc ggcaggcgca     900
ctgaagtctc cgcttctact cgaattgtct ggagttggaa accctgacat cctctcgagg     960
cacggcatcg atacgaagat aaacctgcca accattggcg agaatctcca agatcaaatg    1020
aacaacggac tcgcttacac ctccaagaaa aactacacca aggcggcctc ttacgtcgca    1080 taccettcag ccgaagaact ctttacaaac gcgaccacca ttggtgctca acttctgcgc    1140
aaacttcccg catacgcagc tcaggttgct tcagccaatg gtaatgtgac tcgggccgct    1200
gatatcgagc gcttcttcaa gatccagtgg gacttgatct tcaaatctca tatcccagtc    1260
gcagaaatct tgctggagcc atttggtttt acttatgact cggagtattg gggatcggtt    1320
ccattttcgc gtggcagcat tcacatctca tcttctgacc caactgcccc ggccatcatt    1380
gatcctaagt atttcatgtt ggattttgat ttccatgccc aggttgaggc agctcgcttt    1440
```

```
attcgtgagt tgtttaagac tgagccattt gccgatatgg caggtgccga gacaagcccg    1500
ggtctttcag ctgtctcttc caatgctgat gacgaagggt ggtcttcatt cctcaagtct    1560
aacttccgat cgaacttcca ccctatcacc acggctggca tgatgccaaa ggaaattggt    1620
ggtgttgtgg acacttcttt gaaggtctat ggaacttcga atgttcgtgt tgtcgacgcc    1680
tcggtgatcc cattccaggt ttgcggacac ttgcaaagca ctatctacgc ggttgccgag    1740
cgcgcagccg acatcataaa agctcaaatg tag                                 1773

<210> SEQ ID NO 2
<211> LENGTH: 590
<212> TYPE: PRT
<213> ORGANISM: Penicillium lilacinoechinulatum

<400> SEQUENCE: 2
```

| | | | | | | | | | | | | | | | |
|---|---|---|---|---|---|---|---|---|---|---|---|---|---|---|---|
| Met | Arg | Ser | Leu | Ile | Ser | Leu | Ala | Leu | Leu | Pro | Leu | Ala | Ala | Ala | Val |
| 1 | | | | 5 | | | | | 10 | | | | | 15 | |
| Pro | His | Val | Ser | Arg | Ser | Ser | Glu | Thr | Thr | Tyr | Asp | Tyr | Ile | Val | Val |
| | | | 20 | | | | | 25 | | | | | 30 | | |
| Gly | Gly | Gly | Thr | Ser | Gly | Leu | Val | Ile | Ala | Asn | Arg | Leu | Ser | Glu | Leu |
| | | | | 35 | | | | | 40 | | | | | 45 | |
| Glu | Lys | Val | Asn | Val | Leu | Val | Ile | Glu | Ala | Gly | Gly | Ser | Val | Tyr | Asn |
| | 50 | | | | | 55 | | | | | 60 | | | | |
| Asn | Pro | Asn | Val | Thr | Asp | Thr | Ala | Gly | Tyr | Gly | Lys | Ala | Phe | Gly | Thr |
| 65 | | | | | 70 | | | | | 75 | | | | | 80 |
| Asp | Ile | Asp | Trp | Ala | Tyr | Glu | Thr | Val | Lys | Gln | Glu | Trp | Gly | Gly | Gly |
| | | | | 85 | | | | | 90 | | | | | 95 | |
| Thr | Lys | Gln | Thr | Val | Arg | Ala | Gly | Lys | Ala | Leu | Gly | Gly | Thr | Ser | Thr |
| | | | 100 | | | | | 105 | | | | | 110 | | |
| Ile | Asn | Gly | Met | Val | Tyr | Leu | Arg | Ala | Gln | Lys | Ser | Gln | Ile | Asp | Ala |
| | | | | 115 | | | | | 120 | | | | | 125 | |
| Trp | Glu | Lys | Ile | Gly | Asn | Asp | Gly | Trp | Asn | Trp | Lys | Asn | Leu | Phe | Pro |
| | 130 | | | | | 135 | | | | | 140 | | | | |
| Tyr | Tyr | Arg | Lys | Gly | Glu | Lys | Phe | Gln | Val | Pro | Thr | Asp | Tyr | Ala | Phe |
| 145 | | | | | 150 | | | | | 155 | | | | | 160 |
| Leu | Glu | Gly | Thr | Gly | Val | Ala | Tyr | Asp | Pro | Ala | Phe | His | Gly | Tyr | Asn |
| | | | | 165 | | | | | 170 | | | | | 175 | |
| Gly | Pro | Leu | Lys | Val | Gly | Trp | Thr | Ser | Thr | Gln | Leu | Asn | Asp | Gly | Leu |
| | | | 180 | | | | | 185 | | | | | 190 | | |
| Ala | Gln | Val | Met | Asn | Ser | Thr | Tyr | Gln | Asn | Met | Ser | Val | Pro | Val | Pro |
| | | | | 195 | | | | | 200 | | | | | 205 | |
| Tyr | Asn | Lys | Asp | Pro | Asn | Gly | Gly | Gln | Met | Val | Gly | Tyr | Ser | Val | Tyr |
| | 210 | | | | | 215 | | | | | 220 | | | | |
| Pro | Lys | Thr | Val | Asn | Ser | Glu | Leu | Asn | Ile | Arg | Glu | Asp | Ala | Ala | Arg |
| 225 | | | | | 230 | | | | | 235 | | | | | 240 |
| Ala | Tyr | Tyr | Tyr | Pro | Tyr | Gln | Asn | Arg | Thr | Asn | Leu | His | Val | Trp | Leu |
| | | | | 245 | | | | | 250 | | | | | 255 | |
| Asn | Ser | His | Val | Asn | Lys | Leu | Val | Trp | Lys | Asp | Gly | Ala | Asn | Met | Thr |
| | | | 260 | | | | | 265 | | | | | 270 | | |
| Ala | Asp | Gly | Val | Glu | Val | Lys | Phe | Ser | Asn | Gly | Thr | Thr | Ala | Thr | Val |
| | | | | 275 | | | | | 280 | | | | | 285 | |
| Lys | Ala | Ala | Arg | Glu | Val | Ile | Leu | Ala | Ala | Gly | Ala | Leu | Lys | Ser | Pro |
| | 290 | | | | | 295 | | | | | 300 | | | | |
| Leu | Leu | Leu | Glu | Leu | Ser | Gly | Val | Gly | Asn | Pro | Asp | Ile | Leu | Ser | Arg |
| 305 | | | | | 310 | | | | | 315 | | | | | 320 |

-continued

His Gly Ile Asp Thr Lys Ile Asn Leu Pro Thr Ile Gly Glu Asn Leu
            325                 330                 335

Gln Asp Gln Met Asn Asn Gly Leu Ala Tyr Thr Ser Lys Lys Asn Tyr
        340                 345                 350

Thr Lys Ala Ala Ser Tyr Val Ala Tyr Pro Ser Ala Glu Glu Leu Phe
    355                 360                 365

Thr Asn Ala Thr Thr Ile Gly Ala Gln Leu Leu Arg Lys Leu Pro Ala
370                 375                 380

Tyr Ala Ala Gln Val Ala Ser Ala Asn Gly Asn Val Thr Arg Ala Ala
385                 390                 395                 400

Asp Ile Glu Arg Phe Phe Lys Ile Gln Trp Asp Leu Ile Phe Lys Ser
                405                 410                 415

His Ile Pro Val Ala Glu Ile Leu Leu Glu Pro Phe Gly Phe Thr Tyr
            420                 425                 430

Asp Ser Glu Tyr Trp Gly Ser Val Pro Phe Ser Arg Gly Ser Ile His
        435                 440                 445

Ile Ser Ser Ser Asp Pro Thr Ala Pro Ala Ile Ile Asp Pro Lys Tyr
    450                 455                 460

Phe Met Leu Asp Phe Asp Phe His Ala Gln Val Glu Ala Ala Arg Phe
465                 470                 475                 480

Ile Arg Glu Leu Phe Lys Thr Gln Pro Phe Ala Asp Met Ala Gly Ala
                485                 490                 495

Glu Thr Ser Pro Gly Leu Ser Ala Val Ser Ser Asn Ala Asp Asp Glu
            500                 505                 510

Gly Trp Ser Ser Phe Leu Lys Ser Asn Phe Arg Ser Asn Phe His Pro
        515                 520                 525

Ile Thr Thr Ala Gly Met Met Pro Lys Glu Ile Gly Gly Val Val Asp
    530                 535                 540

Thr Ser Leu Lys Val Tyr Gly Thr Ser Asn Val Arg Val Val Asp Ala
545                 550                 555                 560

Ser Val Ile Pro Phe Gln Val Cys Gly His Leu Gln Ser Thr Ile Tyr
                565                 570                 575

Ala Val Ala Glu Arg Ala Ala Asp Ile Ile Lys Ala Gln Met
            580                 585                 590

<210> SEQ ID NO 3
<211> LENGTH: 1779
<212> TYPE: DNA
<213> ORGANISM: Penicillium italicum

<400> SEQUENCE: 3
atgcgcagcc tcatcggtct tgcactgctt ccactagcag ttgcagtccc ccatgcctca      60
cacaagtcag actctaccta tgactacatt attgttggag gtggcaccag tggcctcgtt     120
gttgcaaacc ggttgtccga gcaaaaggac accaccgtcc tcgtgatcga agccggcggc     180
tccgtatata caacccaaa tgtgaccaac actctgggat acggtaaagc gttcggtaca     240
gatattgact gggcctacga acgacagcc caagaacatg ccgtgtggatt cccacaaata     300 gtgcgtgccg gaaaggcact tggaggaaca tcgaccatca acggcatggc ctacctccgt     360
gcccaggcag cccagattga cgcatgggaa accgttggca acaagggctg gaactggaag     420
actctcctcc cctacttcaa gaagagcgag cagttccaag atccggcaaa gtacccattc     480
ttggatggat cgggtgtctc ctttgatccg gcctaccacg gctttactgg gcctttgaag     540
gttggctggt cttcaacaca gctgaacgat ggtctcgctc aaaagttgaa cgctacctac     600

-continued

```
cagagcctcg acgttcctgt tccgtacaac cgggacgcca atagcggaga catggttgga    660
tacagtgtgt atcccaagac agtcaatgct gatctcaaca tccgtgagga tgctgcccgt    720
gccttctatt atccttacca gaacagaaca aacctccacg tctggctcaa cacacacgcc    780
aacaagatta cctggaatga gggcagcgag gccaccgcaa atggtgtcga agtcactctt    840
tccaacggca aaaagacagt ggtgaaggct acccgtgaag tgattctcgc tgctggcgca    900
ttgaaatctc ccgtcctgct cgagctttct ggcgttggaa accccgacat tctttccaag    960
cacgggatta ccaccaagat taacctgcca actgtcggtg aaaacttgca ggaccaaatg   1020
aacaatggcc ttaagttcga gtcaaagaag acctacagta ccgataaggg tagttcctac   1080
gtggcctacc cctcagctga ccagctcttc cccaactcca ccgcgctggg agccgacctt   1140
cttcgcaagc ttcccgctta tgcagcccag gttgcatccg ccaacggcaa catcaccaaa   1200
gcccgcgaca tttaccgctt cttcaagatc cagtgggatt tgatctttaa ggatgaaatt   1260
cctgtcgcag agatcctgct ctcgggctcc ggagcctcat acagcggcga gtactgggt    1320
tctgttccgt tctctcgcgg cagcgttcac ctttcttccg cagacccac ggcggcccct    1380
accattgacc ccaagtactt catgctggac tttgatctcc acgctcaggc acaggcggcg   1440
cggttcattc gtgaaatctt caagaccgag ccacttgctg cacggccgg tgctgaaacc   1500
accccggtc tttctactgt tgctgctggc gctgatgatg aggcctggtc taaatttatc   1560
tacagtaaat accgatcgaa ctaccacccg attaccacag ctggcatgct gcctaaggag   1620
cttggtggtg ttgttgatac ctcgctgaag gtttatggaa cctccaatgt ccgtgttgtg   1680
gatgcttccg tcatgccttt ccaggtctgc ggtcaccttc agagcaccgt gtatgcggtt   1740
gccgagcgcg cggccgatat catcaaggga gagttgtaa                          1779
```

<210> SEQ ID NO 4
<211> LENGTH: 592
<212> TYPE: PRT
<213> ORGANISM: Penicillium italicum

<400> SEQUENCE: 4

```
Met Arg Ser Leu Ile Gly Leu Ala Leu Leu Pro Leu Ala Val Ala Val
1               5                   10                  15

Pro His Ala Ser His Lys Ser Asp Ser Thr Tyr Asp Tyr Ile Ile Val
            20                  25                  30

Gly Gly Gly Thr Ser Gly Leu Val Val Ala Asn Arg Leu Ser Glu Gln
        35                  40                  45

Lys Asp Thr Thr Val Leu Val Ile Glu Ala Gly Ser Val Tyr Asn
    50                  55                  60

Asn Pro Asn Val Thr Asn Thr Leu Gly Tyr Gly Lys Ala Phe Gly Thr
65                  70                  75                  80

Asp Ile Asp Trp Ala Tyr Glu Thr Thr Ala Gln Glu His Ala Gly Gly
                85                  90                  95

Phe Pro Gln Ile Val Arg Ala Gly Lys Ala Leu Gly Gly Thr Ser Thr
            100                 105                 110

Ile Asn Gly Met Ala Tyr Leu Arg Ala Gln Ala Gln Ile Asp Ala
        115                 120                 125

Trp Glu Thr Val Gly Asn Lys Gly Trp Asn Trp Lys Thr Leu Leu Pro
    130                 135                 140

Tyr Phe Lys Lys Ser Glu Gln Phe Gln Asp Pro Ala Lys Tyr Pro Phe
145                 150                 155                 160
```

-continued

Leu Asp Gly Ser Gly Val Ser Phe Asp Pro Ala Tyr His Gly Phe Thr
                165                 170                 175

Gly Pro Leu Lys Val Gly Trp Ser Ser Thr Gln Leu Asn Asp Gly Leu
            180                 185                 190

Ala Gln Lys Leu Asn Ala Thr Tyr Gln Ser Leu Asp Val Pro Val Pro
        195                 200                 205

Tyr Asn Arg Asp Ala Asn Ser Gly Asp Met Val Gly Tyr Ser Val Tyr
    210                 215                 220

Pro Lys Thr Val Asn Ala Asp Leu Asn Ile Arg Glu Asp Ala Ala Arg
225                 230                 235                 240

Ala Phe Tyr Tyr Pro Tyr Gln Asn Arg Thr Asn Leu His Val Trp Leu
                245                 250                 255

Asn Thr His Ala Asn Lys Ile Thr Trp Asn Glu Gly Ser Glu Ala Thr
            260                 265                 270

Ala Asn Gly Val Glu Val Thr Leu Ser Asn Gly Lys Lys Thr Val Val
        275                 280                 285

Lys Ala Thr Arg Glu Val Ile Leu Ala Ala Gly Ala Leu Lys Ser Pro
    290                 295                 300

Val Leu Leu Glu Leu Ser Gly Val Gly Asn Pro Asp Ile Leu Ser Lys
305                 310                 315                 320

His Gly Ile Thr Thr Lys Ile Asn Leu Pro Thr Val Gly Glu Asn Leu
                325                 330                 335

Gln Asp Gln Met Asn Asn Gly Leu Lys Phe Glu Ser Lys Lys Thr Tyr
            340                 345                 350

Ser Thr Asp Lys Gly Ser Ser Tyr Val Ala Tyr Pro Ser Ala Asp Gln
        355                 360                 365

Leu Phe Pro Asn Ser Thr Ala Leu Gly Ala Asp Leu Leu Arg Lys Leu
    370                 375                 380

Pro Ala Tyr Ala Ala Gln Val Ala Ser Ala Asn Gly Asn Ile Thr Lys
385                 390                 395                 400

Ala Arg Asp Ile Tyr Arg Phe Phe Lys Ile Gln Trp Asp Leu Ile Phe
                405                 410                 415

Lys Asp Glu Ile Pro Val Ala Glu Ile Leu Leu Ser Gly Ser Gly Ala
            420                 425                 430

Ser Tyr Ser Gly Glu Tyr Trp Gly Ser Val Pro Phe Ser Arg Gly Ser
        435                 440                 445

Val His Leu Ser Ser Ala Asp Pro Thr Ala Pro Thr Ile Asp Pro
    450                 455                 460

Lys Tyr Phe Met Leu Asp Phe Asp Leu His Ala Gln Ala Gln Ala Ala
465                 470                 475                 480

Arg Phe Ile Arg Glu Ile Phe Lys Thr Glu Pro Leu Ala Asp Thr Ala
                485                 490                 495

Gly Ala Glu Thr Thr Pro Gly Leu Ser Thr Val Ala Ala Gly Ala Asp
            500                 505                 510

Asp Glu Ala Trp Ser Lys Phe Ile Tyr Ser Lys Tyr Arg Ser Asn Tyr
        515                 520                 525

His Pro Ile Thr Thr Ala Gly Met Leu Pro Lys Glu Leu Gly Gly Val
    530                 535                 540

Val Asp Thr Ser Leu Lys Val Tyr Gly Thr Ser Asn Val Arg Val Val
545                 550                 555                 560

Asp Ala Ser Val Met Pro Phe Gln Val Cys Gly His Leu Gln Ser Thr
                565                 570                 575

Val Tyr Ala Val Ala Glu Arg Ala Ala Asp Ile Ile Lys Gly Glu Leu

-continued

```
                580             585             590

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Ile Gly Gly Val Val Asp Thr Ser Leu Lys Val Tyr Gly Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Trp Gly Gly Gly Thr Lys Gln Thr Val Arg Ala Gly Lys Ala Leu Gly
1               5                   10                  15

Gly Thr Ser Thr
            20
```

GLUCOSE DEHYDROGENASE

CROSS-REFERENCE TO RELATED APPLICATIONS

This patent application is a divisional of U.S. patent application Ser. No. 11/694,540, filed on Mar. 30, 2007, now U.S. Pat. No. 7,494,794, which claims priority to U.S. Provisional Patent Application No. 60/788,252, filed on Mar. 31, 2006.

INCORPORATION-BY-REFERENCE OF MATERIAL ELECTRONICALLY SUBMITTED

Incorporated by reference in its entirety herein is a replacement computer-readable nucleotide/amino acid sequence listing submitted concurrently herewith and identified as follows: 15,728 bytes ASCII (Text) file named "704320ReplacementSequenceListing.txt," created Feb. 11, 2009.

TECHNICAL FIELD

The present invention relates to novel glucose dehydrogenase (hereinafter sometimes abbreviated as "GDH") capable of being used for a glucose measurement reagent and a glucose sensor.

BACKGROUND ART

Self-monitoring of blood glucose is important for a patient with diabetes to figure out a usual blood glucose level in the patient and apply it to treatment. An enzyme taking glucose as a substrate is utilized for a sensor used for the self-monitoring of blood glucose. An example of such an enzyme includes, for example, glucose oxidase (EC. 1.1.3.4). Glucose oxidase is advantageous in that it has high specificity for glucose and is excellent in thermal stability, and thus has been used as the enzyme for a blood glucose sensor from a long time ago. Its first publication goes back 40 years ago. In the blood glucose sensor using glucose oxidase, the measurement is performed by transferring electrons produced in a process of oxidizing glucose to convert into D-glucono-δ-lactone to an electrode via a mediator. However, glucose oxidase easily transfers protons produced in the reaction to oxygen, and thus dissolved oxygen affects the measured value, which has been problematic.

In order to avoid such a problem, for example, NAD(P)-dependent glucose dehydrogenase (EC. 1.1.1.47) or pyrroloquinoline quinone-dependent glucose dehydrogenase (EC. 1.1.5.2; former EC. 1.1.99.17) is used as the enzyme for the blood glucose sensor. They dominates in that they are not affected by dissolved oxygen, but the former NAD(P)-dependent glucose dehydrogenase has the poor stability and requires the addition of the coenzyme. Meanwhile, the latter PQQ-dependent glucose dehydrogenase is inferior in substrate specificity, reacts with other sugars such as maltose and lactose and thus correctness of the measured value is impaired.

In Patent document 1, flavin-binding type glucose dehydrogenase derived from genus *Aspergillus* has been disclosed. This enzyme dominates in that this is excellent in substrate specificity and is not affected by the dissolved oxygen. For the thermal stability, it has been described that a residual activity ratio after being treated at 50° C. for 15 minutes is about 89% and this enzyme is excellent in thermal stability (hereinafter also described as heat resistance). However, considering the case of requiring the treatment with heat in a step of producing sensor chips, its stability is not always sufficient.

Patent document 1: WO 2004/058958

DISCLOSURE OF THE INVENTION

It is an object of the present invention to overcome shortcomings which publicly known enzymes for a blood glucose sensor as described above have and provide an enzyme for the blood glucose sensor which is practically more advantageous.

As a result of an extensive study for accomplishing the above objects, the present inventors have acquired glucose dehydrogenase from filamentous fungus belonging genus *Penicillium*, and found that the glucose dehydrogenase has more excellent properties than the publicly known enzymes for measuring the blood glucose level.

Thus, the invention comprises the following.

[1] Glucose dehydrogenase characterized by being derived from an eukaryotic organism and keeping 90% or more activity after being treated at 55° C. for 15 minutes in a liquid form compared with the activity before the treatment with heat.

[2] Glucose dehydrogenase characterized by being derived from an eukaryotic organism and keep an activity after being treated at 60° C. for 15 minutes in a liquid form.

[3] The glucose dehydrogenase according to [2] characterized by being derived from the eukaryotic organism and keeping 40% or more activity after being treated at 60° C. for 15 minutes in a liquid form compared with the activity before the treatment with heat.

[4] The glucose dehydrogenase according to any one of [1] to [3] wherein the eukaryotic organism is a filamentous fungus.

[5] The glucose dehydrogenase according to [4] wherein the filamentous fungus is a filamentous fungus belonging to genus *Penicillium*.

[6] The glucose dehydrogenase according to [5] wherein the filamentous fungus belonging to genus *Penicillium* is *Penicillium lilacinoechinulatum* or *Penicillium italicum*.

[7] The glucose dehydrogenase according to any one of [1] to [6] characterized in that an action upon maltose is less than 1% of an action upon glucose.

[8] The glucose dehydrogenase according to [7] characterized in that the action upon galactose is less than 2% of the action upon glucose.

[9] Glucose dehydrogenase derived from an eukaryotic organism and having the following physicochemical properties (a) to (f):

(a) optimum reaction temperature: 50° C.;

(b) optimum reaction pH: about 6.5;

(c) temperature stability: a residual activity ratio of GDH after being treated at 55° C. for 15 minutes is 90% or more and the residual activity ratio of GDH after being treated at 60° C. for 15 minutes is 40% or more;

(d) pH stability: 5.0 to 8.0 (the residual activity ratio of GDH after being treated at 25° C. for 16 hours is 90% or more);

(e) substrate specificity: when an action upon glucose is 100%, the action upon xylose is about 10%, the action upon 2-deoxy-D-glucose is about 14%, and a reactivity to maltose, fructose, arabinose, sucrose, galactose, mannose, melezitose, sorbose, ribose, maltotriose, maltotetraose and trehalose is less than 2%; and (f) effects of chemicals: strongly inhibited by cupper, silver and cadmium and inhibited by monoiodoacetic acid, N-ethyl maleimide, hydroxylamine and sodium azide.

[10] Glucose dehydrogenase derived from an eukaryotic organism and having the following physicochemical properties (a) to (f):

(a) optimum reaction temperature: 60° C.;

(b) optimum reaction pH: about 6.5;

(c) temperature stability: a residual activity ratio of GDH after being treated at 55° C. for 15 minutes is 95% or more and the residual activity ratio of GDH after being treated at 60° C. for 15 minutes is 70% or more;

(d) pH stability: 5.0 to 8.0 (the residual activity ratio of GDH after being treated at 25° C. for 16 hours is 80% or more;

(e) substrate specificity: when an action upon glucose is 100, the action upon xylose is about 10%, the action upon 2-deoxy-D-glucose is about 17%, and a reactivity to maltose, fructose, arabinose, sucrose, galactose, mannose, melezitose, sorbose, ribose, maltotriose, maltotetraose and trehalose is less than 2%; and (f) effects of chemicals: strongly inhibited by cupper, silver and cadmium and inhibited by iron, zinc, monoiodoacetic acid, N-ethyl maleimide and hydroxylamine.

[11] A protein corresponding to any of the following (a) to (e):

(a) a protein composed of an amino acid sequence represented by SEQ ID NO:2, and having a glucose dehydrogenase activity;

(b) a protein having consecutive multiple amino acid residue deletions at an N terminal side in the range in which the glucose dehydrogenase activity is not lost in the amino acid sequence represented by SEQ ID NO:2;

(c) a protein having 15 or more and 22 or less consecutive amino acid residue deletions at the N terminal side in the amino acid sequence represented by SEQ ID NO:2;

(d) a protein composed of an amino acid sequence having one or more amino acid residue deletions, substitutions, insertions or additions in the amino acid sequence represented by any of (a) to (c) and having the glucose dehydrogenase activity; and (e) a protein having 80% or more homology to the amino acid sequence represented by SEQ ID NO:2 and having the glucose dehydrogenase activity.

[12] A protein corresponding to any of the following (a) to (e)

(a) a protein composed of an amino acid sequence represented by SEQ ID NO:4, and having a glucose dehydrogenase activity;

(b) a protein having consecutive several amino acid residue deletions at an N terminal side in the range in which the glucose dehydrogenase activity is not lost in the amino acid sequence represented by SEQ ID NO:4;

(c) a protein having 15 or more and 19 or less consecutive amino acid residue deletions at the N terminal side in the amino acid sequence represented by SEQ ID NO:4;

(d) a protein composed of an amino acid sequence having one or more amino acid residue deletions, substitutions, insertions or additions in the amino acid sequence represented by any of (a) to (c) and having the glucose dehydrogenase activity; and (e) a protein having 80% or more homology to the amino acid sequence represented by SEQ ID NO:4 and having the glucose dehydrogenase activity.

[13] A method for producing glucose dehydrogenase by culturing an eukaryotic organism, extracting and purifying the glucose dehydrogenase according to any of [1] to [12].

[14] A nucleic acid having a base sequence encoding the protein according to any of [1] to [12].

[15] A recombinant plasmid connecting a nucleic acid having a base sequence encoding the protein according to any of [1] to [12] under a functional promoter in a host organism.

[16] A recombinant microorganism obtained by transforming a host microorganism with a nucleic acid molecule having a sequence comprising the nucleic acid according to [14].

[17] The recombinant microorganism according to [16] wherein the nucleic acid molecule is the recombinant plasmid according to [15].

[18] The recombinant microorganism according to [16] or [17] wherein the host microorganism is an eukaryotic microorganism.

[19] The recombinant microorganism according to [16] or [17] wherein the host microorganism is a prokaryotic microorganism.

[20] The recombinant microorganism according to [19] wherein the prokaryotic microorganism is a gram-negative bacterium.

[21] The recombinant microorganism according to [20] wherein the gram-negative bacterium is *Escherichia coli*.

[22] A method for producing glucose dehydrogenase by culturing the microorganism according to any of [16] to [21], extracting and purifying the glucose dehydrogenase.

[23] A method for measuring a glucose concentration using the glucose dehydrogenase according to any of [1] to [12].

[24] A glucose assay kit comprising the glucose dehydrogenase according to any of [1] to [12].

[25] A glucose sensor comprising the glucose dehydrogenase according to any of [1] to [12].

According to the present invention, it is possible to provide glucose dehydrogenase which is excellent in heat resistance and substrate specificity and is not affected by dissolved oxygen.

BEST MODES FOR CARRYING OUT THE INVENTION

Figure 1:
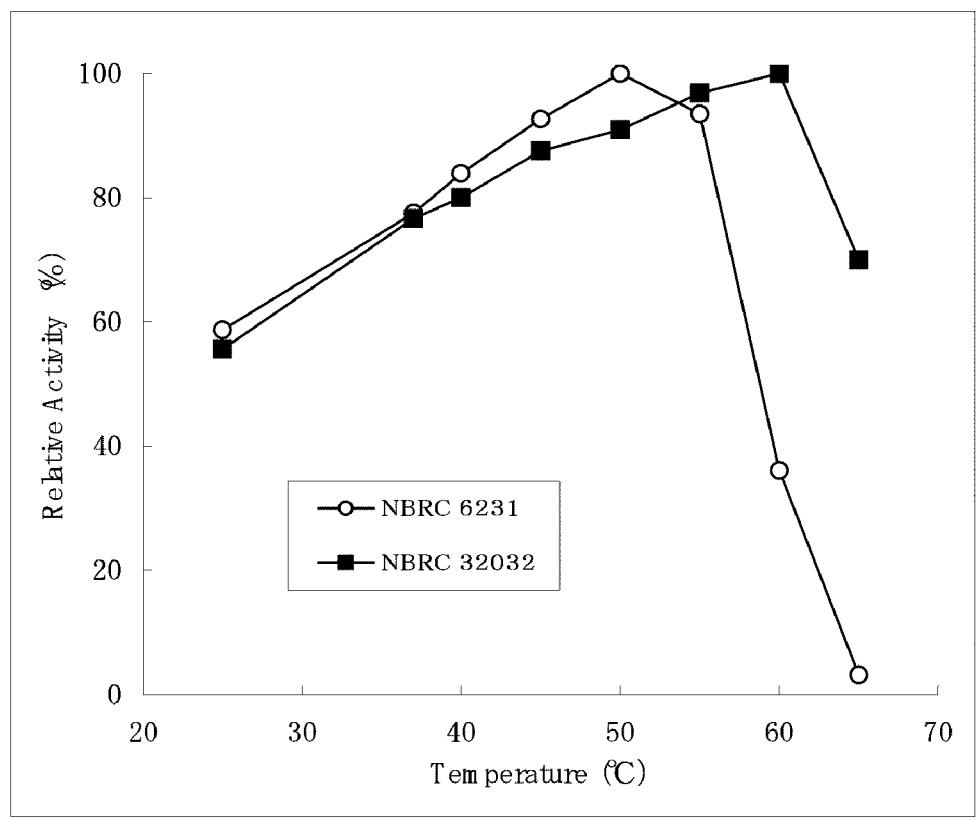
FIG. 1 is a graph showing temperature dependency of reaction rates of GDH of the present invention. A relative activity (%) was shown when the maximum activity was made 100.

The present invention is glucose dehydrogenase derived from an eukaryotic organism and catalyzes the following reaction:

D-Glucose+Electron transport substance (oxidation type) →D-glucono-δ-lactone+Electron transport substance (reduction type).

The present invention is characterized by high heat resistance, and is distinguished in this point from publicly known GDH derived from the eukaryotic organisms. In glucose dehydrogenase derived from *Aspergillus terreus* described to be excellent in stability among publicly known GDH derived from the eukaryotic organisms, a residual activity (activity residual ratio when the activity before being treated with heat is 100%) after being treated with heat at 55° C. for 15 minutes is 60% or less. On the contrary, in GDH of the present invention, the residual activity after being treated at 55° C. for 15 minutes is 90% or more. In GDH of the present invention, preferably the GDH activity is kept after the treatment at 60° C. for 15 minutes and more preferably the residual activity after the treatment at 60° C. for 15 minutes is 40% or more.

When it is determined whether having the aforementioned heat resistance or not, in the present invention, GDH is dissolved in 20 mM K-phosphate buffer (pH 6.5) so as to have the activity of 1 U/mL, and heated for 15 minutes. The activity was measured by a method shown in Test Example described later.

GDH of the present invention could be derived from the eukaryotic organism, and all organisms having a cell nucleus covered with a nuclear membrane are included in a category of the eukaryotic organism. More preferably, the eukaryotic organisms are a filamentous fungi. Among them, preferable filamentous fungi include microorganisms belonging to genera *Penicillium* and *Aspergillus*, and furthermore, it is more preferable to be derived from filamentous fungi belonging to genus *Penicillium*. Moreover, among genus *Penicillium*, it is more preferable that GDH of the present invention is derived from *Penicillium lilacinoechinulatum* or *Penicillium italicum*. These fungal strains are easily available by asking an assignment to the culture collection for respective fungi. The fungal strains registered as the deposit numbers NBRC6231 and NBRC32032 at Biological Resource Center, National Institute of Technology and Evaluation are more preferable as *Penicillium lilacinoechinulatum* and *Penicillium italicum*, respectively.

The present invention is also characterized by high substrate specificity, the action upon maltose is less than 1% of the action upon glucose, and the action upon galactose is less than 2% of the action upon glucose. The action referred to herein indicates the GDH activity at a substrate concentration of 4 mM, it is measured according to Test Example described later, and in a reaction solution composition used, for the substrate concentration, the final concentration is adjusted to 4 mM.

From another viewpoint, the present invention is glucose dehydrogenase derived from the eukaryotic organism and having the following properties.

(a) Apparent molecular weight by gel filtration: about 270 kDa;
(b) optimum reaction temperature: 50° C.;
(c) optimum reaction pH: about 6.5;
(d) temperature stability: residual activity ratio of GDH after being treated at 55° C. for 15 minutes is 90% or more and the residual activity ratio of GDH after being treated at 60° C. for 15 minutes is 40% or more;
(e) pH stability: 5.0 to 8.0 (the residual activity ratio of GDH after being treated at 25° C. for 16 hours is 90% or more);
(f) substrate specificity: when an action upon glucose is 100, the action upon xylose is about 10%, the action upon 2-deoxy-D-glucose is about 14%, and a reactivity to maltose, fructose, arabinose, sucrose, galactose, mannose, melezitose, sorbose, ribose, maltotriose, maltotetraose and trehalose is less than 2%; and
(g) effects of chemicals: strongly inhibited by cupper, silver and cadmium and inhibited by monoiodoacetic acid, N-ethyl maleimide, hydroxylamine and sodium azide.

The eukaryotic organism which GDH is derived from is not particularly limited as long as it can produce GDH having the above properties, is preferably filamentous fungus, more preferably filamentous fungus belonging to genus *Penicillium*, and still more preferably *Penicillium lilacinoechinulatum*. More preferably, the eukaryotic organism is the fungal strain registered as the deposit number NBRC6231 at Biological Resource Center, National Institute of Technology and Evaluation.

Furthermore, the present invention is glucose dehydrogenase derived from the eukaryotic organism and having the following properties.

(a) Apparent molecular weight by gel filtration: 79 to 93 kDa;
(b) optimum reaction temperature: 60° C.;
(c) optimum reaction pH: about 6.5;
(d) temperature stability: residual activity ratio of GDH after being treated at 55° C. for 15 minutes is 95% or more and the residual activity ratio of GDH after being treated at 60° C. for 15 minutes is 70% or more;
(e) pH stability: 5.0 to 8.5 (the residual activity ratio of GDH after being treated at 25° C. for 16 hours is 80% or more);
(f) substrate specificity: when an action upon glucose is 100, the action upon xylose is about 10%, the action upon 2-deoxy-D-glucose is about 17%, and a reactivity to maltose, fructose, arabinose, sucrose, galactose, mannose, melezitose, sorbose, ribose, maltotriose, maltotetraose and trehalose is less than 2%; and
(g) effects of chemicals: strongly inhibited by cupper, silver and cadmium and inhibited by iron, zinc, monoiodoacetic acid, N-ethyl maleimide and hydroxylamine.

The eukaryotic organism which GDH is derived from is not particularly limited as long as it can produce GDH having the above properties, is preferably filamentous fungus, more preferably filamentous fungus belonging to genus *Penicillium*, and still more preferably *Penicillium italicum*. More preferably, the eukaryotic organism is the fungal strain registered as the deposit number NBRC32032 at Biological Resource Center, National Institute of Technology and Evaluation.

When it is determined whether having the aforementioned pH stability or not, in the present invention, GDH is dissolved in 20 mM acetate buffer (pH 4.5 to 6.0), PIPES buffer (pH 6.0 to 7.5) or Tris hydrochloride buffer (pH 7.0 to 8.5) so as to have the activity of 1 U/mL, and heated for 15 minutes. The activity was measured by a method shown in Test Example described later.

A condition for the aforementioned gel filtration is as follows. A column TSK-GEL G3000SW (7.5 mm×300 mm) supplied from Tosoh Corporation and a buffer 50 mM Tris-HCl 150 mM NaCl (pH 7.5) are used. An amount of a sample to be charged is 25 μL, which is then fractionated at a flow rate of 0.5 mL/minutes. Based on a standard curve previously prepared using standard protein solutions, the molecular weight is calculated from a peak position of the sample. A peak position may be specified by monitoring based on ultraviolet absorbance measurement or collecting a fraction from the column and determining a peak of the GDH activity in the fraction.

In the measurement for the effect of the chemicals shown above, each chemical is dissolved at a final concentration of 2 mM in a reaction reagent shown in Test Example described later, and the activity is measured using 0.1 to 5 U/mL GDH solution according to the method in Test Example and compared with the activity measured by a reaction reagent to which the chemical has not been added. "Being inhibited" in the present invention refers to observing 10% or more activity lowering in the case where the chemical has been added compared with the case where the chemical has not been added in the present method. "Undergoing the strong inhibition" refers to observing 50% or more activity lowering in the case where the chemical has been added compared with the case where the chemical has not been added in the present method.

From another viewpoint, the present invention is the protein composed of the amino acid sequence represented by SEQ ID NO:2 and having the glucose dehydrogenase activity. The protein having one or more amino acid substitutions, deletions, insertions or additions in the amino acid sequence represented by SEQ ID NO:2 and having the glucose dehydrogenase activity is also included in the present invention. The protein having 80% or more homology, more preferably 85% or more homology and still more preferably 90% or more homology to the amino acid sequence represented by SEQ ID NO:2 is in the category of the present invention. Furthermore, amino acid residues in these sequences may undergo various modifications, e.g., addition of a sugar chain or methylation in the process of expression.

Furthermore, the present invention is the protein composed of the amino acid sequence represented by SEQ ID NO:4 and having the glucose dehydrogenase activity. The protein having one or more amino acid substitutions, deletions, insertions or additions in the amino acid sequence represented by SEQ ID NO:4 and having the glucose dehydrogenase activity is also included in the present invention. The protein having 80% or more homology, more preferably 85% or more homology and still more preferably 90% or more homology to the amino acid sequence represented by SEQ ID NO:4 is in the category of the present invention. Furthermore, amino acid residues in these sequences may undergo various modifications, e.g., addition of a sugar chain or methylation in the process of expression.

The GDH of the present invention is also the protein which has deleted multiple consecutive amino acid residues at the N-terminal side in the range in which the glucose dehydrogenase activity is not lost in the amino acid sequence represented by SEQ ID NOS:2 and 4. A number of the amino acid residues to be deleted is not particularly limited as long as the GDH activity is not lost. An exemplified target is, for example, the protein in which the N terminal sequence corresponding to the signal sequence or the N terminal sequence predicted to correspond to the signal sequence has been deleted. In the production of GDH not by gene recombination or the recombinant GDH production using the host having the same secretory expression mechanism as in the organism which the GDH was derived from, it is thought that the resulting GDH is mature GDH in which the secretory signal has been eliminated, and that in its amino acid sequence, the portion corresponding to the signal sequence at the N terminal side has been deleted in the amino acid sequence represented by SEQ ID NOS:2 and 4. Also in the recombinant GDH production using the host such as prokaryotic organisms having the different nature from the organism which the GDH was derived from, it is possible to express the gene in which the portion encoding the amino acid sequence corresponding to the signal sequence or predicted to correspond to the signal sequence has been eliminated. At that time, when a terminal amino acid residue after deleting the sequence to be deleted is one other than methionine, it is preferable to add an initial codon (ATG). Alternatively, it is also possible to make GDH with deleted N-terminus by connecting a tag gene through an adaptor to the N terminal sequence to be deleted and digesting the adaptor site with site directed peptidase after the expression. As the method for predicting such an N terminal region, various tools for predicting the signal peptide can be used, and an example of such tools is SignalP var. 3.0. It is possible to access the server (cbs.dtu.dk/services/SignalP/) of this program and predict on line. The signal sequence portion predicted by this method corresponds to either the initial codon to Ala at position 15 or the initial codon to Ser at position 22 in the SEQ ID NO:2, and either the initial codon to Ala at position 15 or the initial codon to Ala at position 19 in SEQ ID NO:4. In particular, when the recombinant GDH is expressed using the prokaryotic organism as the host, it is advantageous that by deleting the above N terminal region, the GDH activity in the culture is enhanced compared with the case of not deleting it.

The "homology" described in the present invention means a percentage (%) of the identical amino acid residues in overlapped all amino acid residues in an optimal alignment when two amino acid sequences are aligned using mathematical algorism publicly known in the art (preferably, the algorism can consider to introduce a gap to one or both of the sequences for the optimal alignment). The homology described in the present invention was calculated using BLAST program incorporating the algorism described in Non-patent literature 1.

Non-patent literature 1: Karlin et al., Proc. Natl. Acad. Sci. USA (1993) Vol. 90, pp. 5873-5877.

GDH composed of the sequence represented by SEQ ID NO:2 and GDH composed of the sequence represented by SEQ ID NO:4 are identical in characteristic of high stability for the heat. The amino acid sequences of these two GDH are 80% homologous, which is extremely high. According to search results in NCBI-BLAST, no amino acid sequence having more than 55% homology to these GDH sequences has been know until now. Therefore, one of indicators which characterize GDH of the present invention can include the high homology to the amino acid sequence represented by SEQ ID NO:2 or 4. It can be presumed that the protein having 80% or more, more preferably 85% or more and still more preferably 90% or more homology is industrially advantageous.

The present invention also provides the method for producing glucose dehydrogenase by culturing the eukaryotic microorganism, and extracting and purifying GDH having the above properties. The eukaryotic microorganism includes filamentous fungi, yeast and eukaryotic algae, is not particularly limited as long as it has the above properties in this range, but is preferably filamentous fungus, more preferably filamentous fungus belonging to genus *Penicillium*, and still more preferably *Penicillium lilacinoechinulatum* or *Penicillium italicum*. Fungal strains corresponding to these species belonging to the genus can be used for the present invention, but more preferably it is better to use *Penicillium lilacinoechinulatum* NBRC6231 or *Penicillium italicum* NBRC32032.

A medium for culturing the microorganism is not particularly limited as long as the microorganism can grow and produce GDH shown in the present invention, but more suitably is preferably one containing carbon sources, inorganic nitrogen sources and/or organic nitrogen sources required for the growth of the microorganism, and more preferably is a liquid medium suitable for ventilation stirring. In the case of the liquid medium, as the carbon sources, for example, glucose, dextran, glycerol, soluble starch and sucrose are exemplified, and the nitrogen sources, for example, ammonium salts, nitrates, amino acids, corn steep liquor, peptone, casein, meat extracts, defatted soy beans and potato extracts are exemplified. As desired, other nutrients (e.g., inorganic salts such as calcium chloride, sodium dihydrogen phosphate and magnesium chloride, and vitamins) may be contained.

The culture is performed according to the method known in the art. For example, spores or growing microbial cells of the microorganism are inoculated in the liquid medium containing the above nutrients, and the microbial cells are grown by leaving stand or ventilation stirring, and preferably the microorganism may be cultured by ventilation stirring. A pH value in the culture medium is preferably 5 to 9 and more preferably 6 to 8. A temperature is typically 14 to 42° C. and preferably 20 to 40° C. The culture is continued typically for 14 to 144 hours, but preferably may be terminated when the amount of expressed GDH is maximized in various culture conditions. As a tactic for finding such a time point, the change of GDH activity is monitored by sampling the culture medium and measuring the GDH activity, and the time point when the increase of GDH activity with time is stopped is regarded as a peak of the activity, and the culture may be terminated.

As the method for extracting GDH from the above culture medium, when GDH accumulated in the microbial cells, only the microbial cells are collected by centrifugation or filtration, and resuspended in a solvent, preferably water or buffer. GDH in the microbial cells can be extracted in the solvent by disrupting the resuspended microbial cells by the publicly known method. As the method for disruption, lytic enzyme can be used, or the method for physically disrupting may be used. The lytic enzyme is not particularly limited as long as it has a capacity to digest a fungal cell wall, and an example of an applicable enzyme includes "lyticase" supplied from Sigma. The method for disrupting physically includes ultrasonic disruption, glass bead disruption and French press. After the disruption, debris can be removed by centrifugation or filtration to yield a GDH extraction solution. When GDH secreted out of the microbial cells is collected, a culture supernatant obtained by centrifuging or filtrating to remove the microbial cells could be made a crude GDH extract to use for the following steps.

As the culture method of the present invention, a solid culture can also be employed. Preferably, the eukaryotic microorganism having a GDH producing capacity of the present invention is grown on a bran such as wheat under an appropriate control of temperature and humidity. At that time, the culture may be performed by leaving stand, or may be mixed by stirring. GDH is extracted by adding the solvent, preferably the water or the buffer to the culture to dissolve GDH and removing solid matters such as microbial cells and bran.

It is also possible to produce GDH of the present invention by cloning (or chemically synthesizing) the nucleic acid (hereinafter described as a GDH gene) encoding the GDH protein and isolating/purifying GDH from the culture of a transformed microorganism containing an expression vector bearing the nucleic acid or inserting the nucleic acid in genomic DNA by recombination.

Cloning of an enzyme gene can be performed according to the publicly known methods. A desired enzyme is completely or partially purified from tissue or cells producing the enzyme, and an amino acid sequence at the N terminus is determined by Edman analysis and mass spectrometry. The amino acid sequence is likewise determined for peptides obtained by partially digesting the enzyme using site specific endopeptidase. Using an oligonucleotide having a base sequence corresponding to the amino acid sequence determined in this way as a probe, the gene is cloned from cDNA library or genomic library by colony (or plaque) hybridization. As the probe, a GDH gene partial sequence amplified by PCR with genomic DNA or cDNA from the organism producing the enzyme as the template using the above oligonucleotide as the primer may be used. Alternatively, the base sequence of the full length gene may be determined by determining flanking sequences of the above partial sequence by inverse PCR method or RACE method and the portion corresponding to the GDH gene may be amplified by PCR. Alternatively, the gene may be cloned by screening the genomic DNA or cDNA with an antibody using the antibody against the enzyme or a partially digested product thereof.

The nucleic acid encoding the GDH of the present invention is the nucleic acid encoding a polypeptide composed of the amino acid sequence represented by SEQ ID NO:2 or 4 or a peptide which is substantially identical thereto. Examples of such a nucleic acid sequence include the sequences represented by SEQ ID NOS:1 and 3, and further the sequence encoding the portion corresponding to the signal sequence may be deleted in the polypeptide. Alternatively, the nucleic acid sequence may be substituted with other codons encoding the identical or similar amino acids throughout the sequence, or when introduced into the eukaryotic host such as filamentous fungi, insect cells or animal cells, the sequence corresponding to the intron may be inserted. Also, the nucleic acid encoding the GDH of the present invention can include the nucleic acid comprising the base sequence which hybridizes the base sequence complementary to the base sequence represented by SEQ ID NO:1 or 3 under a stringent condition and encoding the protein having substantially the same nature as in the protein having the amino acid sequence represented by SEQ ID NO:2 or 4. Those skilled in the art can easily select the stringent condition by changing the temperature in the hybridization reaction and the washing and salt concentrations in a hybridization reaction solution and a washing solution. Specifically, the condition where the hybridization is performed in 6×SSC (0.9 M NaCl, 0.09 M trisodium citrate) or 6×SSPE (3M NaCl, 0.2 M $NaH_2PO_4$, 20 mM EDTA 2Na, pH 7.4) at 42° C. and further the washing is performed with 0.5×SSC at 42° C. is included as one example of the stringent condition of the present invention, but the stringent condition is not limited thereto. Preferably, the condition where the hybridization is performed in 50% formamide, 6×SSC (0.9 M NaCl, 0.09 M trisodium citrate) or 6×SSPE (3 M NaCl, 0.2 M $NaH_2PO_4$, 20 mM EDTA 2Na, pH 7.4) at 42° C. and further the washing is performed with 0.1×SSC at 42° C. is included. The nucleic acid may be DNA or RNA, or DNA/RNA chimera, but preferably is DNA. When the nucleic acid is RNA, the exemplified base sequences are read by changing "t" to "u".

The present invention also provides a nucleic acid molecule comprising the nucleic acid encoding the GDH of the present invention. As such a nucleic acid molecule, a recombinant vector obtained by inserting the GDH gene into a plasmid vector or a viral vector can be exemplified. The recombinant vector of the present invention preferably can keep its replication or autonomically replicate in the host cells, but this is the case of intending to introduce the desired nucleic acid in the genomic DNA, and the recombinant plasmid is not always necessary to replicate in the host cells. The vector suitable for a recombinant expression system of the host of the prokaryotic and/or eukaryotic cells can be used. It is preferable that the vector preferably has a restriction enzyme site at a controllable site downstream of a functional promoter in the host cell. It is possible to ligate the above GDH gene using an appropriate restriction enzyme and ligase, or if necessary a linker or an adaptor DNA. Alternatively, if the GDH gene is a gene fragment amplified using DNA polymerase such as Taq polymerase which adds one base to an amplified end, it is also possible to connect the GDH gene to the vector by TA cloning.

For the purpose of enhancing the solubility of a target protein expressed in the culture or making it easy to purify the GDH protein from the culture medium, a reporter gene and a tag sequence may be connected with the GDH gene in the nucleic acid molecule. Examples of such a sequence include a glutathione-S-transferase gene, a maltose-binding protein gene and 6×His tag. A spacer sequence may be further inserted between these genes or the tag sequence and the GDH gene.

The vectors used for the present invention include, but are not limited to, for example, pBR322, pUC18, pBluescript and SK(−) for *Escherichia coli*, pSH19 and pSH15 for yeast, and pUB110 and pTP5 for *Bacillus subtilis*. Examples of the functional promoter in the host cell include, but are not limited to, for example, trp promoter and lac promoter for *Escherichia coli*, GAP promoter and AGH promoter for yeast, and SPO1 promoter and penp promoter for *Bacillus subtilis*. It is also preferable that the plasmid contains a selection marker gene for selecting transformants, and examples of such a marker gene include resistance genes to antibiotics typified by ampicillin, kanamycin, tetracycline, chloramphenicol and hygromycin, or genes which compensate auxotrophic mutation in the host.

As the host into which the produced nucleic acid molecule is introduced, insect cells, animal cells and plant cells can be used in addition to cells from the microorganisms such as bacteria, Actinomycetes, yeast and filamentous fungi, but preferably the host is the microorganism. The method for transformation can be performed according to the method publicly known in the art, is not particularly limited, and can be performed by electroporation. In addition, competent cells obtained by treating with a cell wall lytic enzyme or a chemical can be used. When the nucleic acid molecule is introduced using them, the nucleic acid molecule is mixed with the competent cells, and the mixture are incubated, or a heat shock is given to the mixture.

The transformed microorganism is cultured in accordance with the above method for culturing the microorganism. In order to selectively grow only the transformed microorganism, preferably, the medium in which the antibiotic corresponding to the marker gene has been added or the minimum medium in which a substance corresponding to the compensated auxotrophy has been removed is used to refine the culture. When GDH is produced by the culture, in order to intensify the expression of the GDH, it is possible to add an expression-inducing substance corresponding to each promoter, or give the suitable temperature condition if the promoter is induced by the temperature condition. The GDH can be extracted from the culture medium after the culture according to the above method for extracting the GDH from the culture of the eukaryotic microorganism.

The GDH can be purified by appropriately combining various separation technologies typically used depending on the fraction in which the GDH activity is detected. The GDH can be purified from the above GDH extraction solution by appropriately selecting the method from publicly known separation methods such as salting out, solvent precipitation, dialysis, ultrafiltration, gel filtration, unmodified PAGE, SDS-PAGE, ion exchange chromatography, hydroxyapatite chromatography, affinity chromatography, reverse phase high performance liquid chromatography and isoelectric focusing electrophoresis. In particular, when the tag is added to the GDH, the column having the affinity to the tag can be used. For example, when the 6×His tag is added, it is possible to easily enhance the purity of the GDH by the use of a nickel column.

It is also possible to add various stabilizing agents into the extracted GDH solution or the purified GDH solution. Examples of such a substance can include, for example, sugars and sugar alcohols typified by mannitol, trehalose, sucrose, sorbitol, erythritol and glycerol, amino acids typified by glutamic acid and arginine, and proteins and peptides typified by bovine serum albumin, ovalbumin and various chaperons. These substances may be used alone or two or more may be appropriately selected and used simultaneously.

The GDH of the present invention can be provided in a liquid form, but can be powderized by lyophilization, vacuum drying or spray drying. At that time, the GDH can be dissolved in the buffer, and it is preferable to further add sugars/sugar alcohols, amino acids, proteins and peptides as excipients or the stabilizing agents. The GDH can be further granulated after being powderized.

The composition of the buffer used for the extraction, purification and powderization of the GDH described above is not particularly limited, could be those having a buffer capacity in the range at pH 5 to 8, and for example, buffers such as Tris hydrochloride and potassium phosphate, and Good's buffers such as BES, Bicine, Bis-Tris, CHES, EPPS, HEPES, HEPPSO, MES, MOPS, MOPSO, PIPES, POPSO, TAPS, TAPSO, TES and Tricine are included.

According to the invention, glucose can be measured in a variety of methods as shown below.

Glucose Assay Kit

The present invention is characterized by the glucose assay kit containing GDH according to the present invention. The glucose assay kit of the present invention contains GDH according to the present invention in a sufficient amount for at least one assay. Typically, the kit includes the buffer, the mediator essential for the assay in addition to GDH, glucose standard solutions for making the calibration curve and instructions for the use. The GDH according to the present invention can be provided in various forms, for example, as the lyophilized reagent or as the solution in the appropriate storage solution.

Glucose Sensor

The present invention is also characterized by the glucose sensor using the GDH according to the present invention. As an electrode, a carbon electrode, a gold electrode, a platinum electrode and the like are used, and the enzyme of the present invention is immobilized on this electrode. As the method for immobilization, the method of using a crosslinking reagent, the method of enfolding in a polymer matrix, the method of covering with a dialysis membrane, photo-crosslinkable polymers, conductive polymers and redox polymers are available. Alternatively, the GDH together with the mediator may be fixed in the polymer or absorbed/fixed on the electrode. Also, the combination thereof may be used. Preferably, the GDH of the present invention is immobilized on the electrode as the holoenzyme, or it is possible to immobilize as the apoenzyme and supply the coenzyme as another layer or in the solution. Typically, the GDH of the present invention is immobilized on the carbon electrode using glutaraldehyde, and subsequently glutaraldehyde is blocked by treating with the reagent having the amine group.

The glucose concentration can be measured as follows. The buffer is placed in a cell at constant temperature, the mediator is added and the temperature is kept constant. As an action electrode, the electrode on which GDH of the present invention has been immobilized is used, and a counter electrode (e.g., platinum electrode) and a reference electrode (e.g., Ag/AgCl electrode) are used. A certain voltage is applied to the carbon electrode and the current becomes constant, and subsequently the increase of the current is measured by adding the sample containing glucose. According to the calibration curve made from the glucose solutions at standard concentrations, the glucose concentration in the sample can be calculated.

The mediator used for the composition for measuring the glucose level, the glucose assay kit, the glucose sensor or the method for measuring the glucose level is not particularly limited, and is preferably 2,6-dichlorophenol-indophenol (abbreviated as DCPIP) and ferrocene or derivatives thereof (e.g., potassium ferricyanide, phenazine methosulfate) could be used. As these mediators, commercially available products can be obtained.

Test Example

In the present invention, the glucose dehydrogenase activity is measured under the following condition.

<Reagents>

50 mM PIPES buffer pH 6.5 (including 0.1% Triton X-100)

14 mM 2,6-dichlorophenol-indophenol (DCPIP) solution

1 M D-glucose solution.

A reaction reagent is made by mixing 15.8 mL of the PIPES buffer, 0.2 mL of the DCPIP solution and 4 mL of the D-glucose solution.

<Measurement Condition>

The reaction reagent (2.9 mL) is preliminarily heated at 37° C. for 5 minutes. The GDH solution (0.1 mL) is added and gently mixed, subsequently the change of absorbance at 600 nm is recorded for 5 minutes using a spectrophotometer controlled to 37° C. using water as a control, and the change of absorbance per one minute ($\Delta OD_{TEST}$) is calculated from a linear portion of the record. The solvent in which GDH will be dissolved in place of the blinded GDH solution is added to the reagent mixture, and the change of absorbance ($\Delta OD_{BLANK}$) per one minute is measured. The GDH activity is calculated from these values according to the following formula. One unit (U) in the GDH activity is defined as the amount of the enzyme which reduces 1 μmol DCPIP for one minute in the presence of 200 mM D-glucose.

Activity (U/mL)=[—($\Delta OD_{TEST}$–$\Delta OD_{BLANK}$)×3.0× dilution scale]/(16.3×0.1×1.0)

In the above formula, 3.0 represents a liquid amount (mL) of the reaction reagent+the enzyme solution, 16.3 represents a millimolar molecular absorbance coefficient (cm²/μmol) in the condition of measuring the present activity, 0.1 represents the liquid amount of the enzyme solution (mL) and 1.0 represents a light path length (cm) of the cell.

EXAMPLES

The present invention will be more specifically described below by Examples, but the present invention is not limited to the following Examples.

Example 1

Acquisition of GDH Derived from Filamentous Fungi Belonging to Genus *Penicillium*

Using *Penicillium lilacinoechinulatum* NBRC6231 and *Penicillium italicum* NBRC32032 (purchased from Independent Administrative Institution, National Institute of Technology and Evaluation) as fungi producing GDH, the respective lyophilized fungi were inoculated on a potato dextrose agar medium (supplied from Difco) and incubated at 25° C. to restore. Fungal threads restored on the plate were collected including the agar, which was then suspended in filtrated sterilized water. A production medium (1% malt extract, 1.5% soy bean peptide, 0.1% MgSO$_4$.7H$_2$O, 2% glucose, pH 6.5) was prepared in two 10 L jar fermenters and sterilized by autoclave at 120° C. for 15 minutes. Then, the above fungal thread suspension was added thereto, and the culture was started. The culture was performed under the condition of a temperature at 30° C., a ventilation amount at 2 L/minute and a stirring frequency at 380 rpm. The culture was stopped 64 hours after the start of the culture, and microbial cells from each fungal strain were collected on filter paper by aspiration filtration using Nutsche filter. The microbial cells were resuspended in 3 L of 20 mM K-phosphate buffer (pH 6.5), and disrupted using French press at a pressure of 130 MPa. A disrupted cell solution was dispensed in a 500 mL centrifuge tube and cell debris was precipitated by centrifuging at 8000 rpm for 15 minutes using a high speed cooling centrifuge supplied from Hitachi Ltd. A supernatant was concentrated to 1/10 amount using a hollow fiber module for ultrafiltration with molecular weight 10,000 cut off, and ammonium sulfate was added to a concentrated solution so that the final concentration was 60% saturation (456 g/L). Subsequently, the mixture was centrifuged at 8000 rpm for 15 minutes using the high speed cooling centrifuge supplied from Hitachi Ltd. to precipitate pellets. Then, the supernatant was absorbed to an Octyl-Sepharose column, and fractions having the GDH activity were collected by eluting with a gradient of ammonium sulfate from 0.6 to 0.0 saturation. Salting out was performed by eluting the resulting GDH solution through a G-25 Sepharose column for gel filtration and collecting protein fractions. Ammonium sulfate corresponding to 0.6 saturation was added to the solution after the salting out. This mixture was absorbed to a Phenyl Sepharose column, and fractions having the GDH activity were collected by eluting with the gradient of ammonium sulfate from 0.6 to 0.0 saturation. This was heated at 50° C. for 45 minutes and centrifuged to yield the supernatant. The solution obtained by the above steps was rendered a purified GDH sample.

Example 2

Estimation of Molecular Weight

The GDH solution (25 μL) derived from NBRC6231 or NBRC32032 purified in Example was applied to TSK-GEL G300SW (7.5 mm×300 mm) supplied from Tosoh Corporation, buffered with Tris-HCl (pH 7.5) and was fractionated at a flow rate of 0.5 mL/minute. For the elution of GDH from NBRC6231, an elution time was determined from a peak appearing position by monitoring the absorbance at 280 nm. For the elution of GDH from NBRC32032, the fractions were collected using a fraction collector, the GDH activity in each fraction was measured according to Test Example, the peak fraction was specified and the time required for the elution was calculated from the peak. Based of the elution time, the molecular weight of the GDH protein was calculated from a standard curve previously made using standard protein solutions (MW-Marker [MW 12,400 to 290,000] supplied from Oriental Yeast Co., Ltd.). As a result, it was estimated that GDH derived from NBRC6231 and GDH derived from NBRC32032 have the molecular weights of about 270 kDa and 79 to 93 kDa, respectively.

Example 3

Optimal Reaction Temperature

In order to know the optimal reaction temperature of the purified GDH solutions derived from NBRC6231 and NBRC32032 obtained in Example 1, by making a preliminary heating temperature and the temperature of the reaction reagent 25, 37, 40, 45, 50, 55, 60 and 65° C., the activity under each condition was measured. FIG. 1 is a graph showing a relative activity when the maximum activity value was made 100. From the above, it has been found that the optimal reaction temperature of GDH derived from NBRC6231 is in the range higher than 45° C. and lower than 55° C. and is about 50° C. and that the optimal reaction temperature of GDH derived from NBRC32032 is in the range higher than 55° C. and lower than 65° C. and is about 60° C.

Example 4

Optimal Reaction pH

Figure 2:
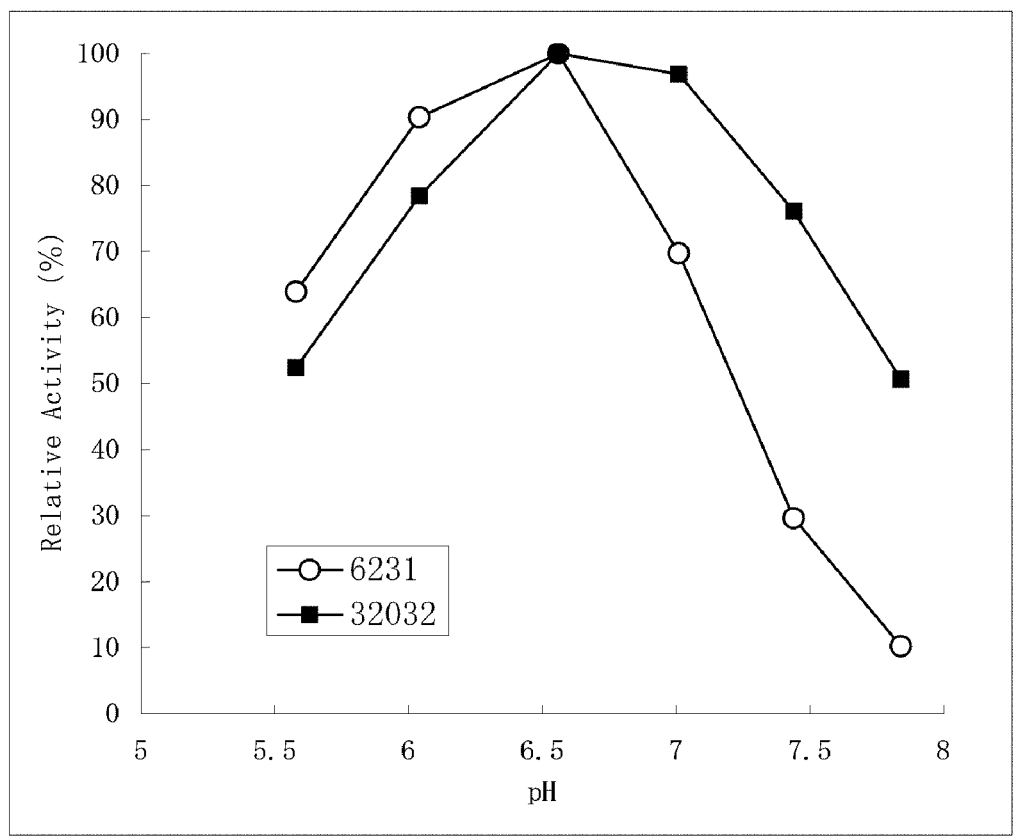
FIG. 2 is a graph showing pH dependency of reaction rates of GDH of the present invention. The relative activity (%) was shown when the maximum activity was made 100.

In order to know the optimal reaction pH of the purified GDH solutions derived from NBRC6231 and NBRC32032 obtained in Example 1, the reaction reagent was prepared using 50 mM K-phosphate buffers in the range from pH 5.5 to 8.0 instead of PIPES buffer in the reagents shown in above Test Example, and the activity was measured using these according to the procedure in Test Example. FIG. 2 is a graph showing the relative activity at each pH when the maximum activity value was made 100. Both GDH derived from NBRC6231 and NBRC32032 exhibited the maximum activity at around pH 6.5. From the above, it has been found that both optimal reaction pH of GDH derived from NBRC6231 and NBRC32032 is in the range higher than 6.0 and lower than 7.0 and is about 6.5.

Example 5

Temperature Stability

Figure 3:
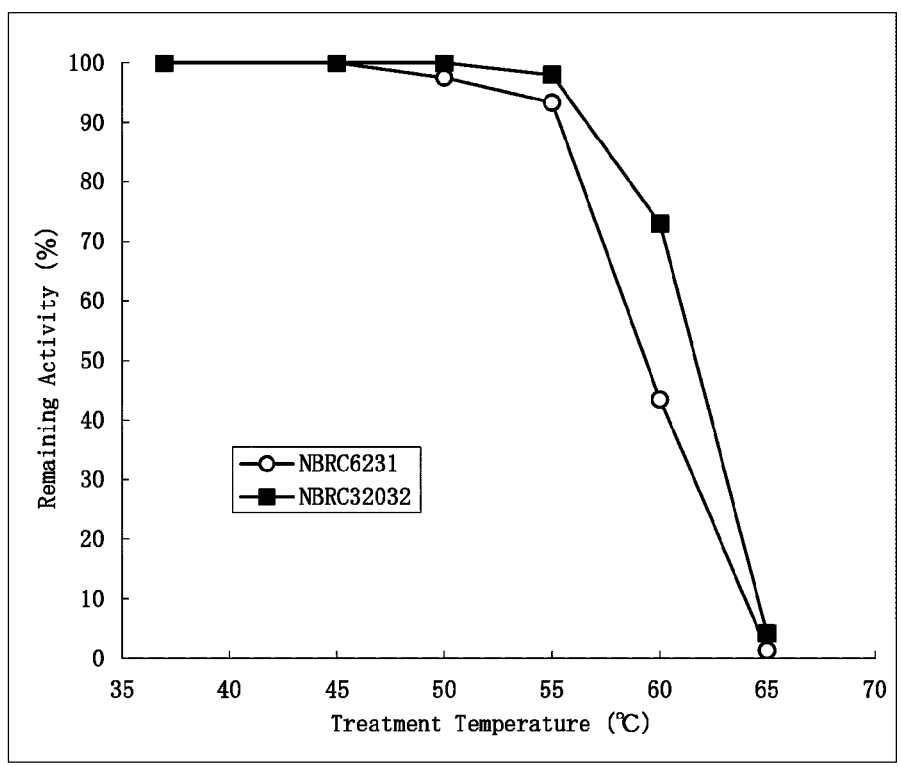
FIG. 3 is a graph showing temperature stability of GDH of the present invention. An activity value after treating with heat at each temperature was represented by the relative activity (%) when the activity before treating with heat was made 100.

In order to know the temperature stability of the purified GDH solutions derived from NBRC6231 and NBRC32032 obtained in Example 1, each GDH solution was diluted to have the activity of 1 U/mL using 20 mM K-phosphate buffer (pH 6.5), this diluted GDH solution was heated at each temperature in the range of 37° C. to 65° C. for 15 minutes using a heat bath, and the activities before and after the treatment were compared. The activity was measured according to Test Example described above. FIG. 3 is a graph showing the residual activity after heating relative to the activity before heating. In GDH derived from NBRC6231, the residual activity was 93% or 44% after being treated at 55° C. or 60° C., respectively. In GDH derived from NBRC32032, the residual activity was 98% or 73% after being treated at 55° C. or 60° C., respectively.

Example 6 pH Stability

Figure 4:
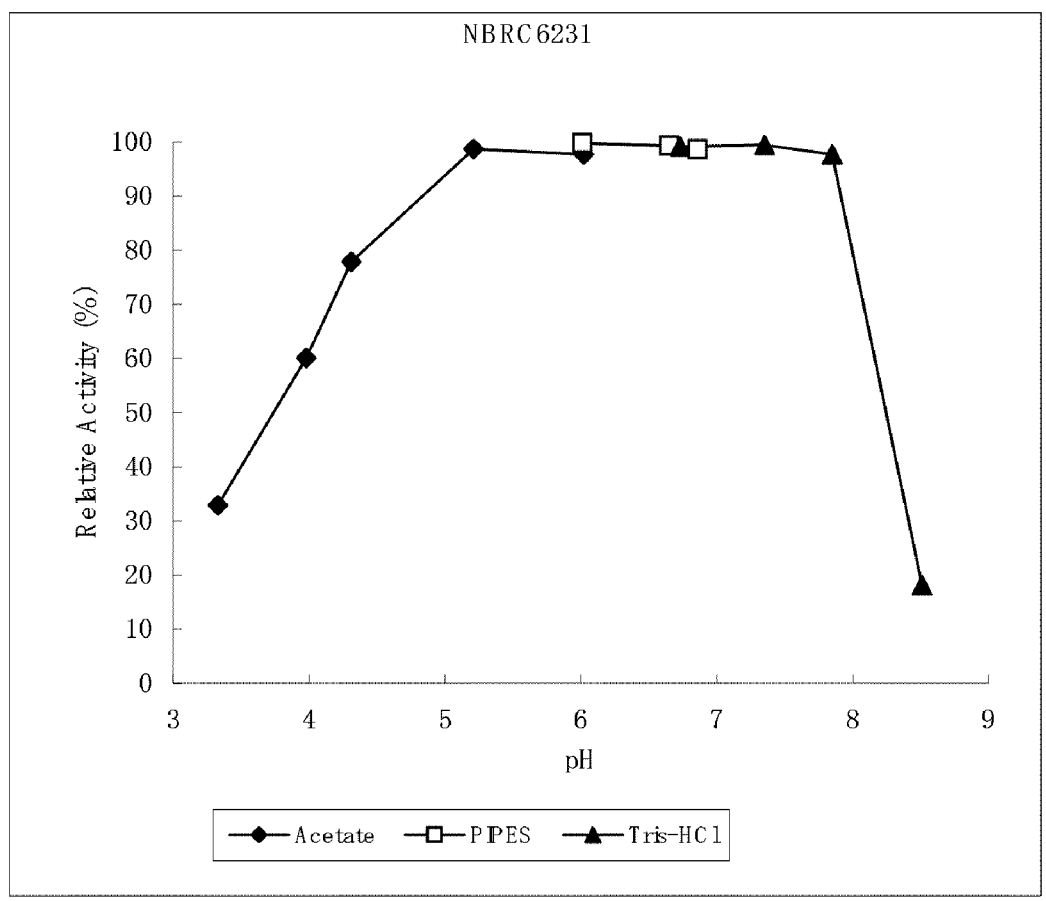
FIG. 4 is a graph showing the pH stability of GDH derived from a deposit number NBRC6092. Acetate buffer, PIPES buffer and Tris hydrochloride buffer were used for pH 3.3 to 6, pH 6 to 7 and pH 7 to 8.5, respectively.
Figure 5:
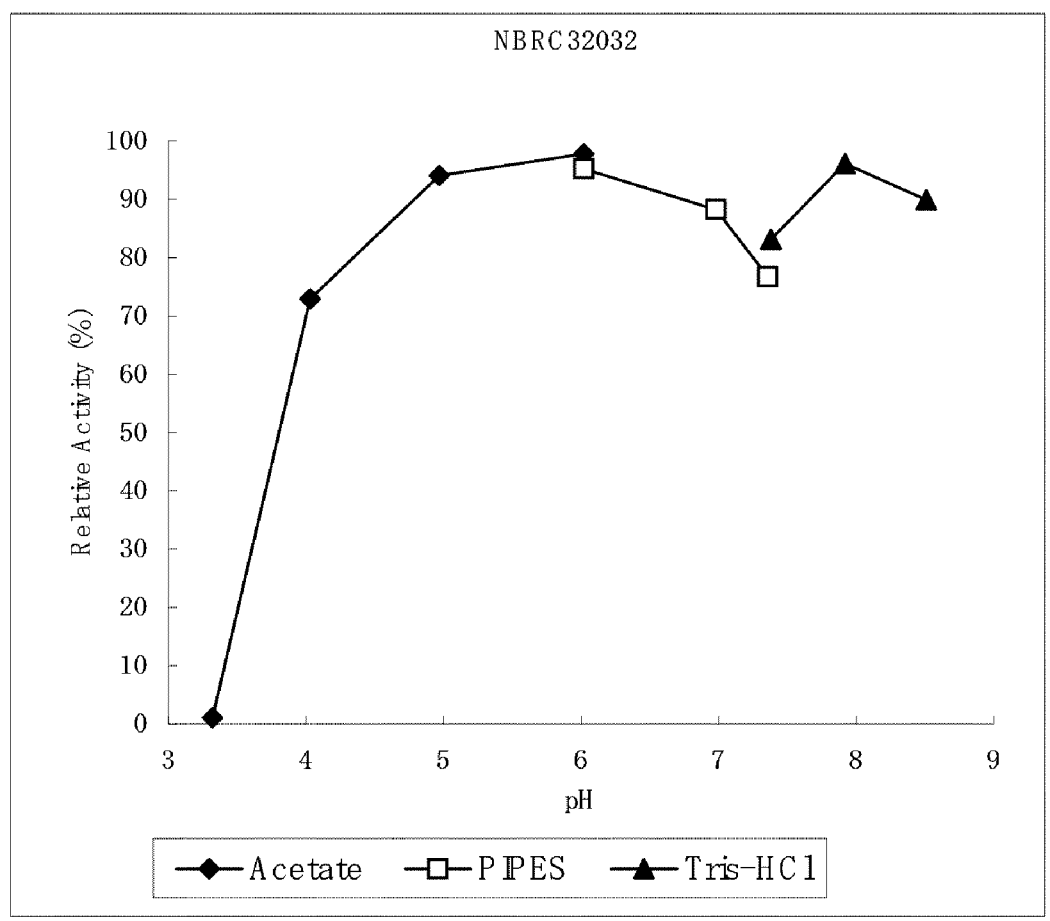
FIG. 5 is a graph showing the pH stability of GDH derived from a deposit number NBRC32032. Acetate buffer, PIPES buffer and Tris hydrochloride buffer were used for pH 3.3 to 6, pH 6 to 7 and pH 7 to 8.5, respectively.

In order to know the pH stability of the purified GDH solutions derived from NBRC6231 and NBRC32032 obtained in Example 1, the buffers for pH 3.3 to 8.5 (pH 3 to 6: acetate buffers, pH 6 to 7: PIPES buffers, pH 7 to 8.5: Tris hydrochloride buffers) were prepared, and using these buffers, each GDH solution was diluted to have the enzyme activity of 1 U/mL. The diluted GDH solution was incubated at 25° C. for 16 hours, and the activities before and after the incubation were compared. FIGS. 4 (derived from NBRC6231) and 5 (derived from NBRC32032) are graphs showing the residual activity after the incubation relative to the activity before the incubation. GDH derived from NBRC6231 exhibited the residual activity of 80% or more in the range of pH 5 to 8 and exhibited the good stability. Meanwhile, GDH derived from NBRC32032 exhibited the residual activity of 80% or more in the range of pH 5 to 8.5, but in the case of PIPES buffer, the residual activity at pH 7.4 was 77%.

Example 7

In order to know the substrate specificity of the purified GDH solutions derived from NBRC6231 and NBRC32032 obtained in Example 1, the activity was measured using the reaction reagent in which the substance shown in Table had been dissolved at a final concentration of 4 mM. Table 1 shows the activity for each substrate when the activity using glucose as the substrate was made 100%. It was found that both enzymes acted upon 2-deoxy-D-glucose and xylose in the substrates other than glucose. But, both enzymes exhibited the reactivity at practically no problematic levels to other sugars.

TABLE 1

| Substrate | Relative activity | |
|---|---|---|
| (Final concentration 4 mM) | NBRC6231 | NBRC32032 |
| Glucose | 100 | 100 |
| Maltose | 0.5 | 0.2 |
| Fructose | 0.2 | 0.3 |
| Arabinose | 0.2 | 0.2 |
| Glycerin | 0.1> | 1.7 |
| Sucrose | 0.6 | 1.1 |
| Melezitose | 0.2 | 0.5 |
| Sorbose | 0.1> | 0.5 |
| Ribose | 0.1> | 0.2 |
| Maltotriose | 0.2 | 1.0 |
| Maltotetraose | 0.1> | 1.6 |
| Galactose | 1.0 | 0.6 |
| Mannose | 1.6 | 0.9 |
| Xylose | 10.1 | 10.4 |
| 2-deoxy-D-glucose | 14.3 | 17.2 |
| Trehalose | 0.3 | 0.1> |

Example 8

In order to know the effects of chemicals on the purified GDH solutions derived from NBRC6231 and NBRC32032 obtained in Example 1, the substance shown in Table 2 was added at a final concentration of 2 mM to the reaction reagent shown in Test Example, and the GDH activity was measured using this. The relative activity when the activity value in the case of adding no chemical was made 100 is shown in Table 2. The substances commonly exhibiting the strong inhibitory effect include copper sulfate, cadmium acetate and silver nitrate. The inhibitory effect was commonly observed in monoiodoacetic acid, N-ethylmaleimide and hydroxylamine. It was also found that GDH derived from NBRC6231 was inhibited by sodium azide and that GDH derived from NBRC32032 was inhibited by iron chloride (III).

TABLE 2

| Additives (Final concentration 2 mM) | Relative activity NBRC6231 | Relative activity NBRC32032 |
|---|---|---|
| $MgCl_2$ | 99.7 | 102 |
| $CaCl_2$ | 103 | 103 |
| $Ba(OAc)_2$ | 106 | 106 |
| $FeCl_3$ | 106 | 77.5 |
| $CoCl_2$ | 94.1 | 102 |
| $MnCl_2$ | 93.4 | 99.1 |
| $ZnCl_2$ | 76.2 | 75.1 |
| $Cd(OAc)_2$ | 41.0 | 41.4 |
| $NiCl_2$ | 96.6 | 101 |
| $CuSO_4$ | 2.2 | 4.5 |
| $AgNO_3$ | 20.9 | 15.0 |
| Monoiodoacetic acid | 68.7 | 73.3 |
| N-ethylmaleimide | 86.8 | 87.8 |
| Iodoacetamide | 111 | 101 |
| Hydroxylamine | 81.5 | 79.1 |
| EDTA | 113 | 104 |
| o-phenanthroline | 106 | 103 |
| α,α'-dipyridyl | 109 | 102 |
| Borate | 111 | 102 |
| NaF | 111 | 102 |
| $NaN_3$ | 89.3 | 97.8 |

Example 9

Km Value for D-Glucose

The activity of GDH derived from NBRC6231 or NBRC32032 was measured by changing D-glucose concentrations in the range of 200 mM or lower in the reaction reagent composition described in Test Example. The Km value was calculated according to Lineweaver-Burk plot method. As a result, GDH derived from NBRC6231 had the Km value of 13 mM and GDH derived from NBRC32032 had the Km value of 7 mM.

Example 10

Application to Glucose Electrode

Figure 6:
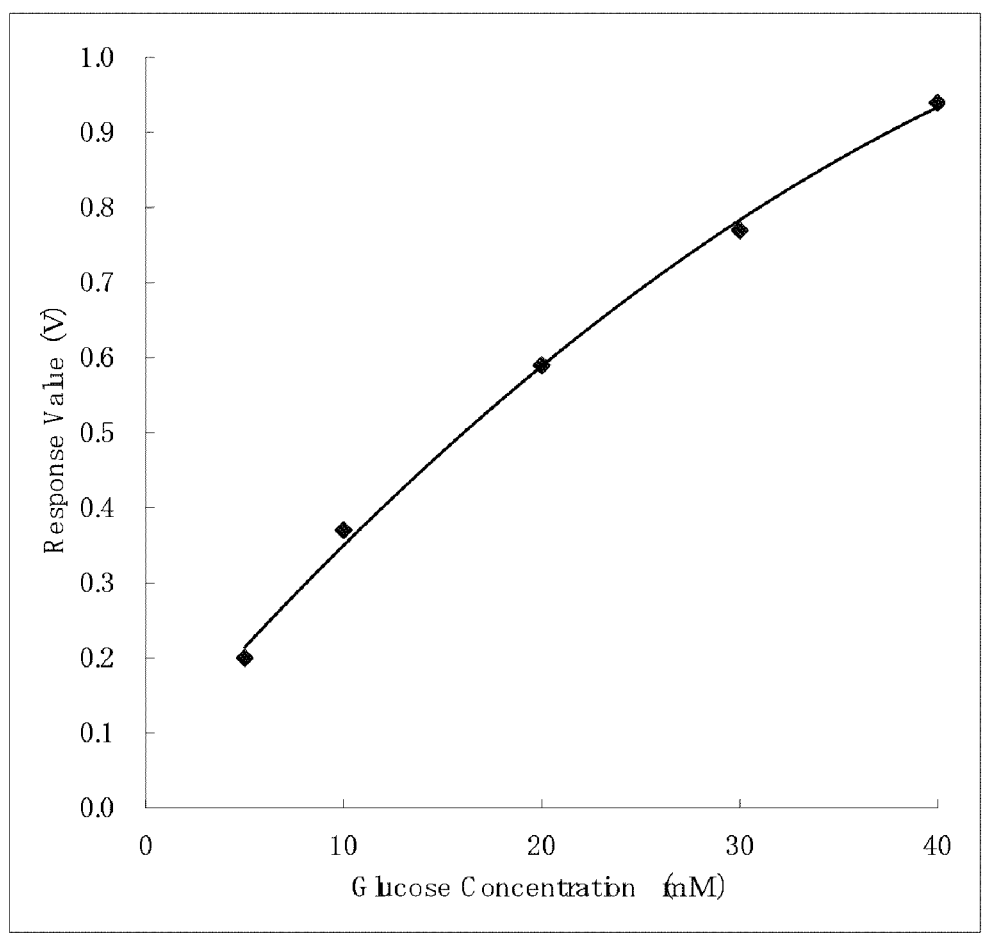
FIG. 6 is a graph showing a relation between glucose concentrations and response voltage values in a glucose electrode made using GDH of the present invention. The response voltage value 1 V output by a detector corresponds to 10 µA of current in the glucose electrode.

Carbon graphite (0.5 g) was placed in a mortar, 0.3 mL of liquid paraffin was added, and the mixture was kneaded using a pestle to make carbon paste. The carbon paste made was kneaded on a platinum electrode, further 10 μL of the purified GDH solution (500 U/mL, derived from the deposit number NBRC6231) made according to Example 1 was added, and they were dried in air at room temperature for 30 minutes. A cellulose semi-permeable membrane for dialysis was placed on the enzyme electrode dried in air, and the semi-permeable membrane was secured with a plastic O-ring. A glucose electrode made in this way was used after immersing in 50 mM potassium phosphate buffer (pH 7.0) previously ice-cooled, for 30 minutes. In a cuvette warmed at 25° C., 20 mL of a reaction solution was placed, the glucose electrode (action electrode), a platinum electrode as the counter electrode and an Ag/AgCl electrode as the reference electrode were immersed therein, and the voltage of +0.35 V was applied. After the current value became constant, glucose was added and the current values which responded thereto were monitored. A detector output by converting 1 μA of the current value into 0.1 V of the voltage, and the change of the output voltage values with time was graphed. A voltage increase from a background value to a steady state value after the addition of glucose was made a response value (V). FIG. 6 is a graph plotting response value obtained at each glucose concentration by changing the concentration of glucose to be added at the final concentration in the range of 5 to 40 mM. From these results, the increase of response values depending on the glucose concentration was observed, and it has been identified that GDH according to the present invention is applicable to the quantification of glucose and usable as the glucose sensors.

Example 11

Preparation of cDNA

For *Penicillium lilacinoechinulatum* strain NBRC6231 and *Penicillium italicum* strain NBRC32032, microorganisms were cultured according to the method in Example 1 (but, the culture in the jar fermenter was performed for 24 hours), and the fungal threads were collected on filter paper using Nutsche filter. The resulting fungal threads were immediately frozen in liquid nitrogen and were disrupted using Cool Mill supplied from Toyobo Co., Ltd. Total RNA was immediately extracted from disrupted microbial cells using Sepasol RNA I supplied from Nacalai Tesque Inc. in accordance with the protocol of this kit. mRNA was purified from the resulting total RNA using Origotex-dt30 (supplied from Daiichi Pure Chemicals Co., Ltd.), and RT-PCR with this as the template was performed using ReverTra-Plus™ supplied from Toyobo Co., Ltd. A resulting product was electrophoresed on agarose gel and a portion corresponding to a chain length of 0.5 to 4.0 kb was cut out. cDNA was extracted from a cut out gel fragment using MagExtractor-PCR&Gel Clean Up supplied from Toyobo Co., Ltd. and purified to use as a cDNA sample.

Example 12

Determination of GDH Gene Sequence

The purified GDH derived from NBRC6231 was dissolved in Tris-HCl buffer (pH 6.8) containing 0.1% SDS and 10% glycerol, and partially digested by adding Glu specific V8 endoprotease at a final concentration of 10 μg/mL thereto and incubating at 37° C. for 16 hours. This sample was electrophoresed on 16% acrylamide gel to separate peptides. Peptide molecules present in this gel were transferred on a PVDF membrane using the buffer for blotting (1.4% glycine, 0.3% Tris and 20% ethanol) by semi-dry method. The peptides transferred on the PVDF membrane were stained using a CBB staining kit (GelCode Blue Stain Reagent supplied from PIERCE), two band portions of the visualized peptide fragments were cut out and internal amino acid sequences were analyzed using a peptide sequencer. The resulting amino acid sequences were IGGVVDTSLKVYGT (SEQ ID NO:5) and WGGGTKQTVRAGKALGGTST (SEQ ID NO:6). Based on this sequence, degenerate primers containing mixed bases were made, and PCR was performed using the cDNA derived from NBRC6231 made in Example 11 as the template. An amplified product was obtained, and was detected as a single band of about 1.4 kb by agarose gel electrophoresis. This band was cut out, and extracted and purified using MagExtractor-PCR&Gel Clean Up supplied from Toyobo Co., Ltd. The purified DNA fragment was TA-cloned using TArget Clone-Plus, and *Escherichia coli* JM 109 competent cells (Competent High JM109 supplied from Toyobo Co., Ltd.) were transformed with the resulting vector by heat shock. Among transformed clones, for colonies in which an insert had been identified by blue-white determination, the plasmid was extracted and purified using MagExtractor-Plasmid by miniprep, and the base sequence of the insert was determined using plasmid sequence specific primers. Based on the determined the partial sequence of the GDH gene, a 5'-flanking region and a 3'-flanking region of the partial sequence were determined by RACE method. The sequence from an initiation codon to a termination codon in the determined gene region is shown in SEQ ID NO:1, and the amino acid sequence deduced from this sequence is shown in SEQ ID NO:2. Likewise, the sequence of the GDH gene derived from NBRC32032 was determined, and its base sequence is shown in SEQ ID NO:3. The amino acid sequence deduced from this sequence is also shown in SEQ ID NO:4. Based on the amino acid sequences deduced from these base sequences, the homology was searched in home page (http://www.ncbi.nlm.nih.gov/BLAST/) of "NCBI BLAST". The GDH sequence derived from NBRC6231 had the highest homology of 55% to glucose oxidase derived from *Botryotinia fuckliana*. The GDH sequence derived from NBRC32032 had the highest homology of 54% to the gene of unnamed protein product (amino acid sequence deduced from ORF) derived from *Aspergillus oryzae*. The homology between GDH derived from NBRC6231 and GDH derived from NBRC32032 was 80%. These two GDH are identical in characteristic that the stability for the heat is high, the homology between the amino acid sequences of these two GDH is extremely high, and it has been found that there is no amino acid sequence publicly known which has the homology of more than 55% thereto. Therefore, one of indicators which characterize the GDH of the present invention includes the high homology to the amino acid sequence represented by SEQ ID NO:2 or 4. It can be presumed that the protein having the homology of 80% or more, more preferably 85% or more and still more preferably 90% or more is industrially advantageous.

Example 13

Preparation of GDH Gene Recombinant Plasmid and Transformed Microorganism

The primers were made by adding NdeI site to 28 bases in 5' end side and adding BamHI site to 28 bases in 3' end side in the base sequence represented by SEQ ID NO:3. Using these primers, PCR with cDNA derived from NBRC32032 as the template was performed. For the amino acid sequence represented by SEQ ID NO:4, the signal sequence in the N terminal sequence was analyzed on the server of SignalP var. 3.0, and it was concluded that the sequence until Ala at position 15 or Ala at position 19 was the potential sequence for the secretory signal. Thus, the primers adding the N terminal restriction enzyme site were made so as to amplify the sequence in which 15 codons (45 bases) in the N terminal region had been deleted and the initiation codon (ATG) had been added and the sequence in which 19 codons (57 bases) at N terminal region had been deleted and the initiation codon (ATG) had been added, and the products amplified by PCR were yielded. The resulting PCR product was electrophoresed on agarose gel and extracted from the gel and purified using MagExtractor-PCR&Gel Clean Up supplied from Toyobo Co., Ltd and purified. Subsequently, the treatment with restriction enzymes, NdeI and BamHI was given. The treated PCR product was mixed with pBluescript KSN(+) given the same treatment with restriction enzymes. They were ligated by adding Ligation High supplied from Toyobo Co., Ltd. in the same amount as the mixed solution and incubating at 16° C. for 30 minutes. A transformed colony was obtained by transforming *Escherichia coli* JM109 strain with the ligated product, applying transformed *Escherichia coli* on LB agar medium containing 50 µg/mL of sodium ampicillin and culturing at 37° C. overnight. A plasmid was extracted by miniprep from a liquid culture product of the colony having the insert, and the base sequence of the insert was identified. In this way, three types of the recombinant plasmids, pPIGDH1 (the full length from the initiation codon of SEQ ID NO:3 had been introduced), pPIGDH2 (the sequence deleting 15 codons in the N terminal region and adding the initiation codon in SEQ ID NO:3 had been introduced), and pPIGDH3 (the sequence deleting 19 codons in the N terminal region and adding the initiation codon in SEQ ID NO:3 had been introduced) were made.

Example 14

Culture of Transformed Microorganisms and Expression of GDH

The recombinant plasmids obtained in Example 13 and the plasmid containing no insert as the control were introduced into *Escherichia coli* C600 strain by electroporation. The resulting transformed strain was inoculated to 5 mL of the LB medium (containing 50 µg/mL of sodium ampicillin) in a test tube, and cultured with shaking at 30° C. for 16 hours. Subsequently 50 µL of this culture medium was added to 5 mL of the LB medium (containing 50 µg/mL of sodium ampicillin), and cultured with shaking at 30° C. for 20 hours. The GDH activity in the culture medium obtained by culturing the transformant with the plasmid containing no insert was subtracted as a blank. The GDH activity in the culture medium of each GDH gene introducing strain was as in Table 3.

TABLE 3

| Plasmid | pPIGDH1 | pPIGDH2 | pPIGDH3 |
|---|---|---|---|
| GDH activity (U/L) | 6.1 | 17.8 | 48.5 |

This way, the expression of the GDH gene in *Escherichia coli* was identified. Furthermore, *Escherichia coli* C600 strain transformed with pPIGDH3 was cultured with shaking in a rich medium (2.4% yeast extract, 2.4% polypeptone, 1.25% dipotassium monohydrogen phosphate, 0.23% monopotassium dihydrogen phosphate, 0.4% glycerol, 50 µg/mL of sodium ampicillin, pH 7.0) at 25° C. for 20 hours, and consequently the activity in the culture medium reached 1,000 U/L.

Example 15

Purification of Expressed Recombinant GDH

*Escherichia coli* C600 strain transformed with pPIGDH3 was inoculated to 60 mL of the LB medium (containing 50 µg/mL of sodium ampicillin) in a 500 mL Sakaguchi flask, and cultured with shaking at 30° C. for 16 hours. This was placed in the rich medium (2.4% yeast extract, 2.4% polypeptone, 1.25% dipotassium monohydrogen phosphate, 0.23% monopotassium dihydrogen phosphate, 0.4% glycerol, 50 µg/mL of sodium ampicillin, pH 7.0) in a 10 L jar fermenter, and cultured at 25° C. with a ventilation amount at 2 L/minute and a stirring rotation frequency at 330 rpm for 24 hours. The cultured microbial cells were collected by centrifugation, suspended in 50 mM phosphate buffer (pH 6.5) so that a microbial cell turbidity at 660 nm was about 50, and disrupted using French press with a pressure of 65 MPa. The nucleic acid was precipitated by adding polyethyleneimine at a final concentration of 9% to the supernatant obtained by centrifuging the disrupted solution, and the supernatant was obtained by centrifugation. Ammonium sulfate in saturated amount was dissolved in this to precipitate an objective protein, and the precipitate collected by centrifugation was re-dissolved in 50 mM phosphate buffer (pH 6.5). Gel filtration using the G-25 Sepharose column and hydrophobic chromatography using the Octyl-Sepharose column and the Phenyl-Sepharose column (a peak fraction was extracted by eluting with ammonium sulfate with concentration gradient from 25% saturation to 0%) were carried out, and further ammonium sulfate was removed by gel filtration using the G-25 Sepharose column to yield a recombinant GDH sample.

Example 16

Application of Expressed Recombinant GDH to Glucose Electrode

Figure 7:
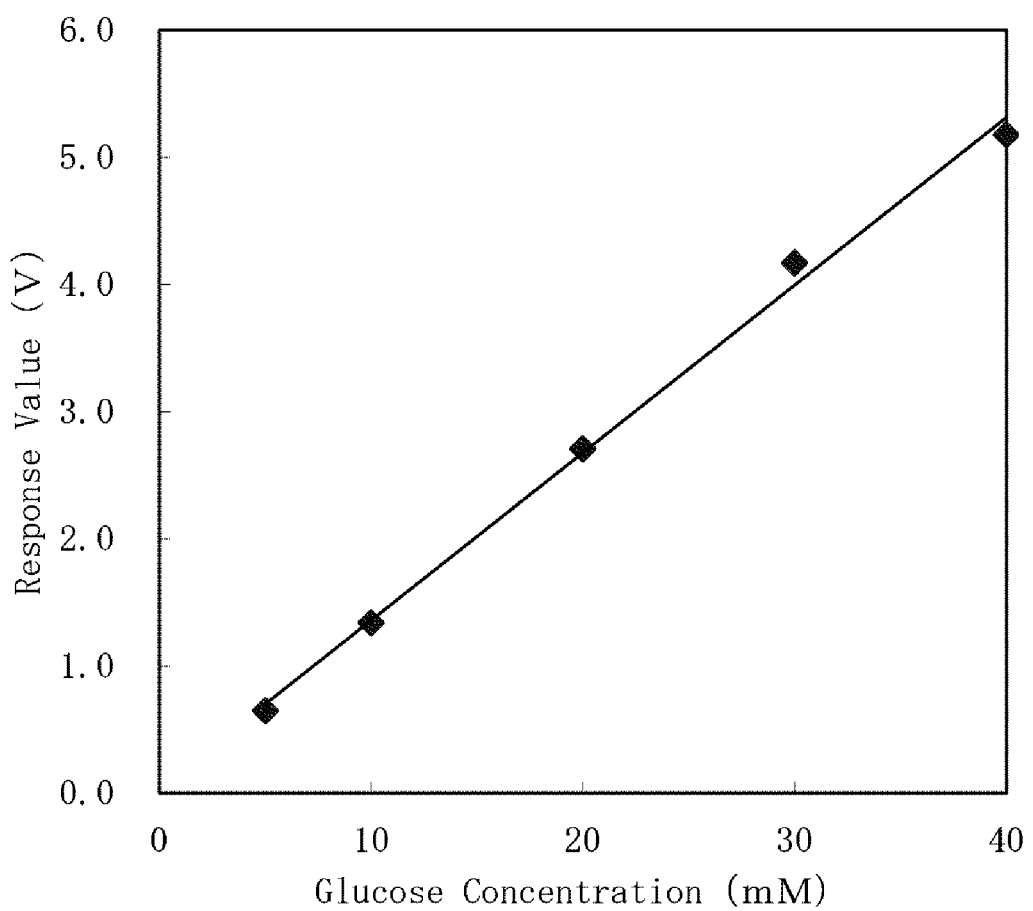
FIG. 7 is a graph showing the relation between glucose concentrations and response voltage values in a glucose electrode made using GDH (recombinant protein) of the present invention. The response voltage value 1 V output by the detector corresponds to 10 µA of current in the glucose electrode.

Using the recombinant GDH obtained in Example 12, in the procedure in Example 10, the glucose electrode was made, and glucose was quantified. The results are shown in FIG. 7. As was shown in the graph, the glucose electrode made using the recombinant GDH also exhibited the responses depending on the glucose concentrations, and was confirmed to be applicable to the quantification of glucose.

INDUSTRIAL APPLICABILITY

According to the present invention, it is possible to obtain the composition for measuring a glucose level or the method for measuring the glucose level. The composition for measuring the glucose level or the method for measuring the glucose level can be used for a glucose assay kit and a glucose sensor.

The invention claimed is:

1. An isolated protein corresponding to any one of the following (a) to (c):
   (a) a protein composed of the amino acid sequence shown in SEQ ID NO: 4 and having glucose dehydrogenase activity;
   (b) a protein having 15 or more and 19 or less amino acid deletions in the N terminal side in the amino acid sequence of SEQ ID NO: 4 and having glucose dehydrogenase activity; and
   (c) a protein having 90% or more homology to the amino acid sequence of SEQ ID NO: 4 and having glucose dehydrogenase activity.

2. The protein of claim 1, wherein the protein is composed of the amino acid sequence shown in SEQ ID NO: 4 and has glucose dehydrogenase activity.

3. The protein of claim 1, wherein the protein has 15 or more and 19 or less amino acid deletions in the N terminal side in the amino acid sequence of SEQ ID NO: 4 and has glucose dehydrogenase activity.

4. The protein of claim 1, wherein the protein has 90% or more homology to the amino acid sequence of SEQ ID NO: 4 and has glucose dehydrogenase activity.

* * * * *